United States Patent [19]

Sterman et al.

[11] Patent Number: 5,718,725
[45] Date of Patent: Feb. 17, 1998

[54] DEVICES AND METHODS FOR INTRACARDIAC PROCEDURES

[75] Inventors: Wesley D. Sterman, San Francisco; Michi E. Garrison, Belmont; Hanson S. Gifford, III, Woodside; John H. Stevens, Palo Alto, all of Calif.

[73] Assignee: Heartport, Inc., Redwood City, Calif.

[21] Appl. No.: 463,814

[22] Filed: Jun. 5, 1995

Related U.S. Application Data

[60] Division of Ser. No. 281,962, Jul. 28, 1994, which is a continuation-in-part of Ser. No. 163,241, Dec. 6, 1993, Pat. No. 5,571,215, which is a continuation-in-part of Ser. No. 23,778, Feb. 22, 1993, Pat. No. 5,452,733.

[30] Foreign Application Priority Data

Dec. 3, 1992 [AU] Australia .................. PL6170

[51] Int. Cl.$^6$ .................. A61F 2/24; A61M 37/00
[52] U.S. Cl. .................. 623/2; 604/5
[58] Field of Search .................. 604/4, 28, 96, 604/206, 205, 16; 623/2, 3, 66

[56] References Cited

U.S. PATENT DOCUMENTS

| | | |
|---|---|---|
| 3,409,013 | 11/1968 | Berry . |
| 3,587,156 | 6/1971 | Shiley . |
| 4,065,816 | 1/1978 | Sawyer . |
| 4,173,981 | 11/1979 | Mortensen . |
| 4,585,453 | 4/1986 | Martin . |
| 4,655,218 | 4/1987 | Kulik et al. . |
| 4,808,163 | 2/1989 | Laub . |
| 4,898,155 | 2/1990 | Ovil et al. . |

(List continued on next page.)

FOREIGN PATENT DOCUMENTS

| | | | |
|---|---|---|---|
| 0218275 | 4/1987 | European Pat. Off. . | |
| 1690738 | 11/1991 | U.S.S.R. | 623/2 |
| 93/20741 | 10/1993 | WIPO . | |

OTHER PUBLICATIONS

Cohn, L. H, et al "Right Thoracotomy, Femorofemoral Bypass, and Deep Hypothermia for Re-Replacement of the Mitral Valve" Soc. of Thoracic Surgeon 1989 pp. 67–71.

Meditech®, Instructions for Use, Occlusion Balloon Catheters Rev. Mar. 1991, pp. 1–7.

Buckberg, G.D. "Strategies and logic of cardioplegic delivery to prevent, avoid, and reverse ischemic and reperfusion damage" *J. Thorac Cardio Vasc Surg*, 93:127–129 (1987).

(List continued on next page.)

*Primary Examiner*—David Isabella
*Attorney, Agent, or Firm*—Townsend and Townsend and Crew LLP

[57] ABSTRACT

The invention provides devices and methods for performing less-invasive surgical procedures within an organ or vessel. In an exemplary embodiment, the invention provides a method of closed-chest surgical intervention within an internal cavity of a patient's heart or great vessel. According to the method, the patient's heart is arrested and cardiopulmonary bypass is established. A scope extending through a percutaneous intercostal penetration in the patient's chest is used to view an internal portion of the patient's chest. An internal penetration is formed in a wall of the heart or great vessel using cutting means introduced through a percutaneous penetration in an intercostal space in the patient's chest. An interventional tool is then introduced, usually through a cannula positioned in a percutaneous intercostal penetration. The interventional tool is inserted through the internal penetration in the heart or great vessel to perform a surgical procedure within the internal cavity under visualization by means of the scope. In a preferred embodiment, a cutting tool is introduced into the patient's left atrium from a right portion of the patient's chest to remove the patient's mitral valve. A replacement valve is then introduced through an intercostal space in the right portion of the chest and through the internal penetration in the heart, and the replacement valve is attached in the mitral valve position.

12 Claims, 25 Drawing Sheets

FIG. 3

U.S. PATENT DOCUMENTS

| | | |
|---|---|---|
| 5,197,979 | 3/1993 | Quintero et al. . |
| 5,203,776 | 4/1993 | Durfee . |
| 5,209,747 | 5/1993 | Knoepfler . |
| 5,236,450 | 8/1993 | Scott . |
| 5,250,038 | 10/1993 | Melker et al. . |
| 5,308,320 | 5/1994 | Safar et al. . |
| 5,383,888 | 1/1995 | Zvenyatsky . |
| 5,391,156 | 2/1995 | Hildwein et al. . |
| 5,433,700 | 7/1995 | Peters .................................... 604/4 |
| 5,531,785 | 7/1996 | Love et al. . |
| 5,011,469 | 4/1991 | Buckberg et al. . |
| 5,032,128 | 7/1991 | Alonso . |
| 5,041,130 | 8/1991 | Cosgrove et al. . |
| 5,104,393 | 4/1992 | Isner et al. . |
| 5,109,859 | 5/1992 | Jenkins . |
| 5,188,619 | 2/1993 | Myers . |

OTHER PUBLICATIONS

Yamaguchi, A., "A case of a reoperation using a ballon catheter with blocked pars ascendes aortae" *Kyobu Geka*, 42(11):961–964 (1991).

Peters, W.S. "The promise of cardioscopic surgery" *AustralAs J Cardiac Thorac Surg.* 2(3):152–154 (1993).

Coltharp et al. "Videothorascopy . . . " *Ann Thorac Surg* 53:776–9 (1992).

Jamieson, W.R.E. "Modern cardiac valve devices–bioprostheses and mechanical prostheses" *J Card Surg* 8:89–98 (1993).

Landreneau et al. "Video–assisted thoracic surgery . . . " *Ann Thorac Surg* 54:800–7 (1992).

Mack et al. "Present role of thoracoscopy in the diagnosis and treatment of diseases of the chest" *Ann Thorac Surg*, 54:403–9 (1992).

Magovern, G.J. "Sutureless aortic and mitral prosthetic valves" *J Thoracic and Cardiovasc Surg,* 48(3):346–361 (1964).

Ozuner et al. "Creation of a pericardial window using thoracoscopic techniques" *Surg, Gynecoloy & Obstetrics*, 175:69–71 (1992).

Wakabayashi, A. "Expanded applications of diagnostic and therapeutic thoracoscopy" *J Thorac and Cardiovasc Surg* 102:721–3 (1991).

Cohn et al. "Right thoracotomy, femorofemoral bypass, and deep hypothermia for re–replacement of the mitral valve," *Ann Thorac Surg,* 48:69–71 (1989).

Fundaro et al. "Towards an easier and safer reoperation of the atrioventricular valves" *J Cardiovasc Surg* 30:779–781 (1989).

Tribble et al. "Anterolateral thoracotomy as an alternative to repeat median sternotomy for replacement of the mitral valve," *Ann Thorac Surg,* 48:380–382 (1987).

Berreklouw et al. "Revival of right thoracotomy to approach atrioventricular valves in reoperations," *Thorac Cardiovasc Surgeon* 32:331–333 (1984).

Cosgrove, D.M. "Management of the calcified aorta: An alternative method of occlusion" *Ann Thorac Surg* 36:718–719 (1983).

Foster and Threlkel "Proximal control of aorta with a balloon catheter" *Surg, Gynecology & Obstetrics* pp. 693–694 (1971).

Erath, Jr. and Stoney, Jr. "Balloon catheter occlusion of the ascending aorta" *Ann Thorac Surg.* 35:560–561 (1983).

Sakaguchi et al. "Aortic valve replacement and coronary artery bypass" *J. Japanese Assoc for Thoracic Surgery* 41(6):1063–1068 (1993).

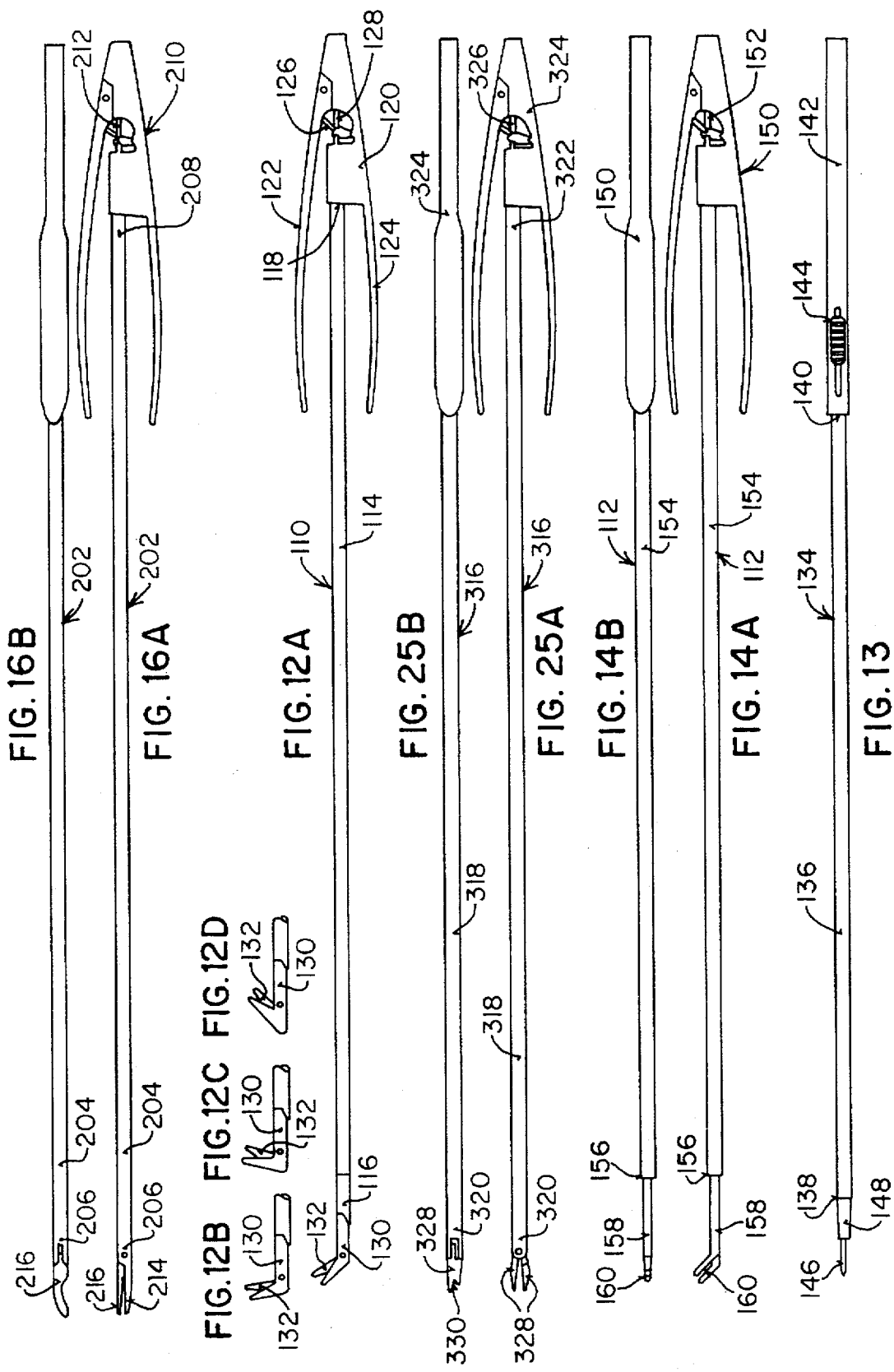

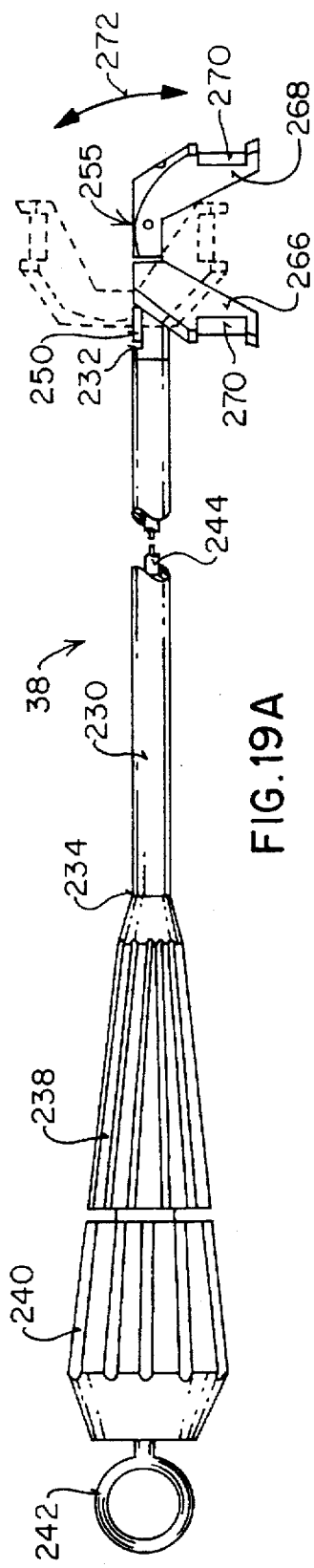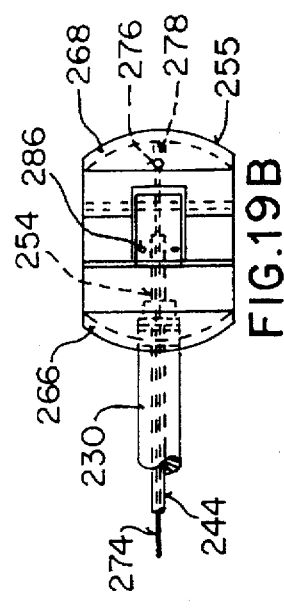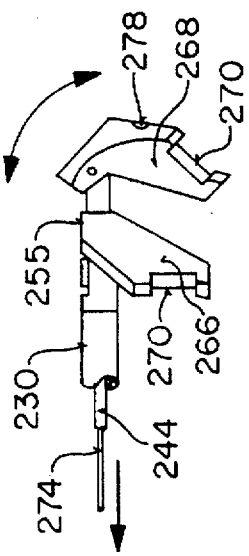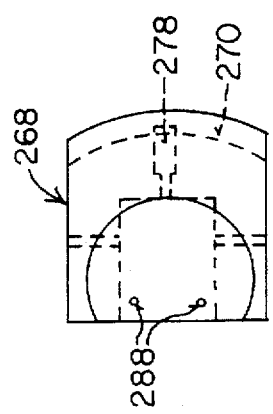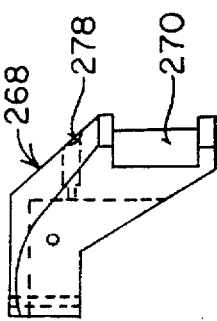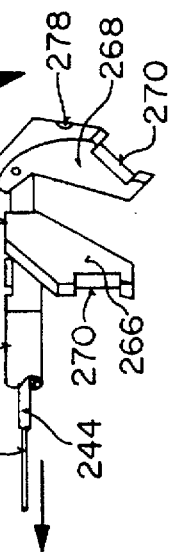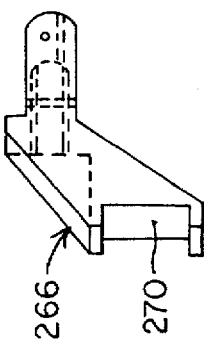

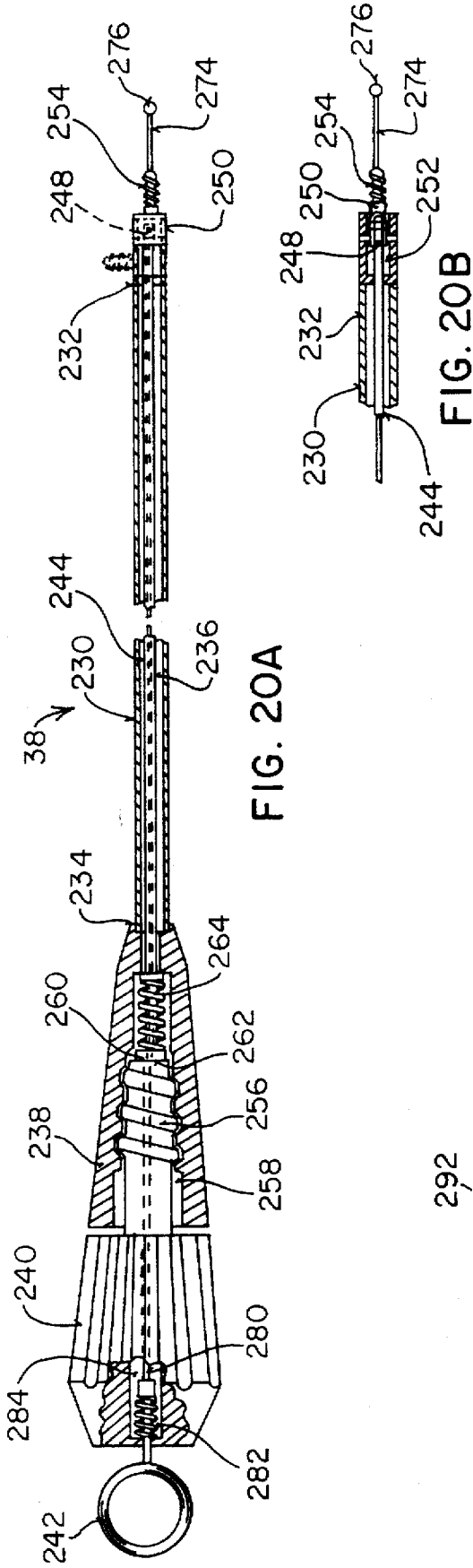
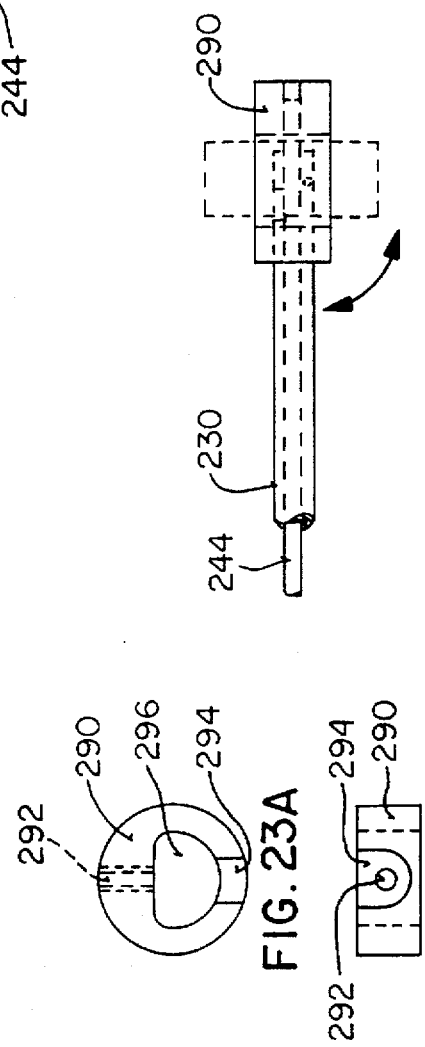
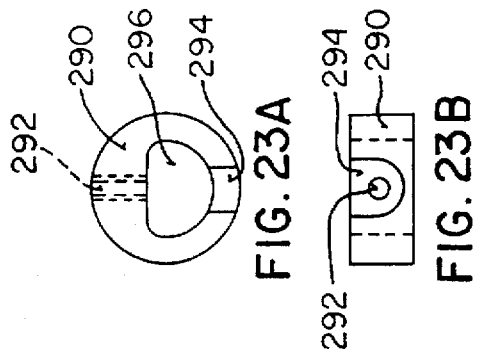
FIG. 20A
FIG. 20B
FIG. 22
FIG. 23A
FIG. 23B

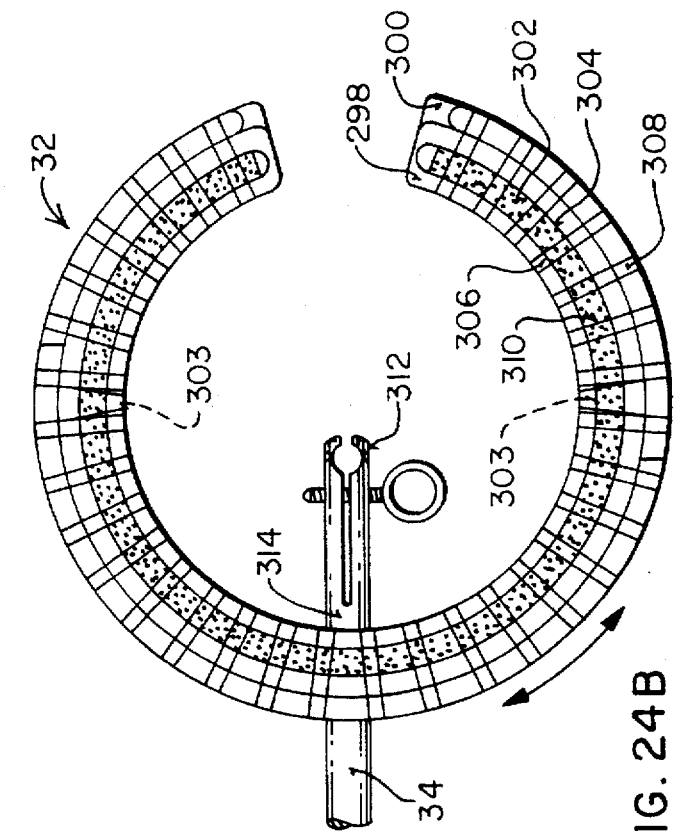
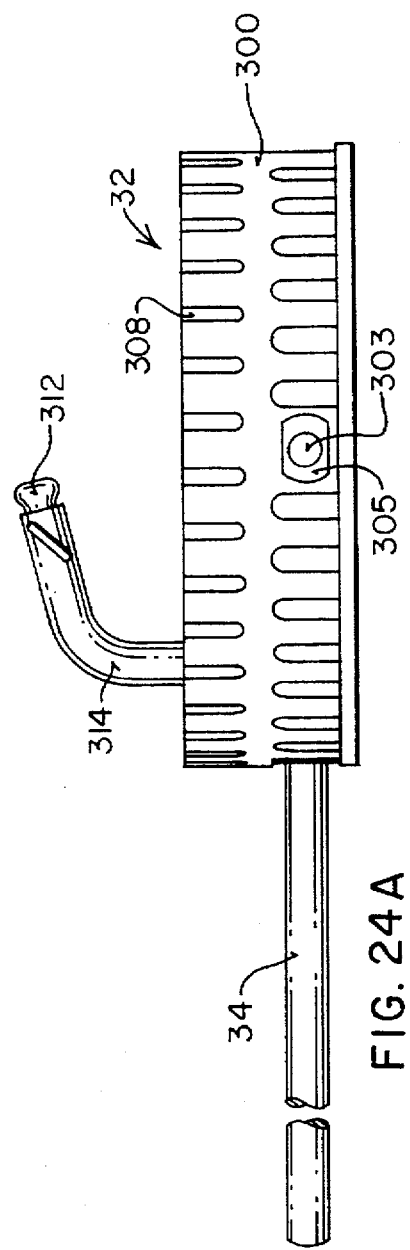
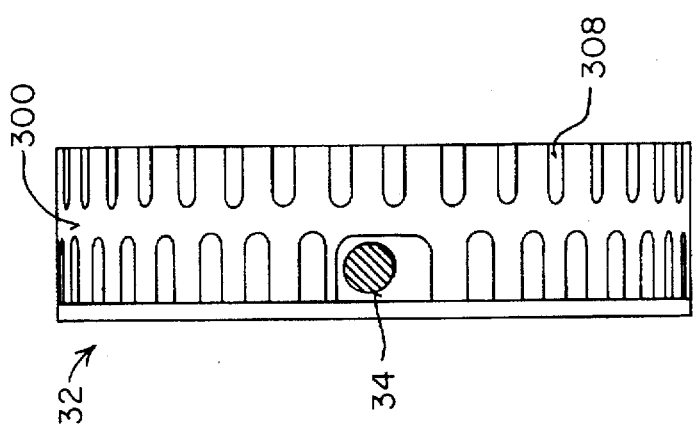
FIG. 24B
FIG. 24A
FIG. 24C

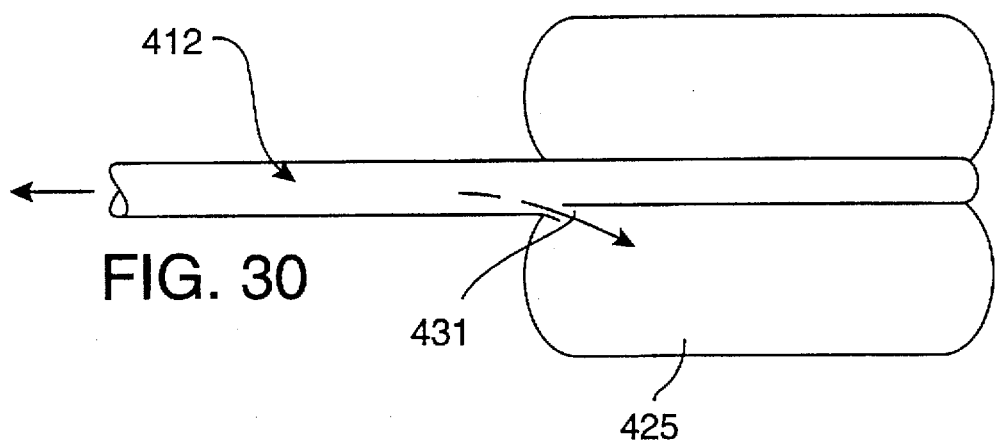
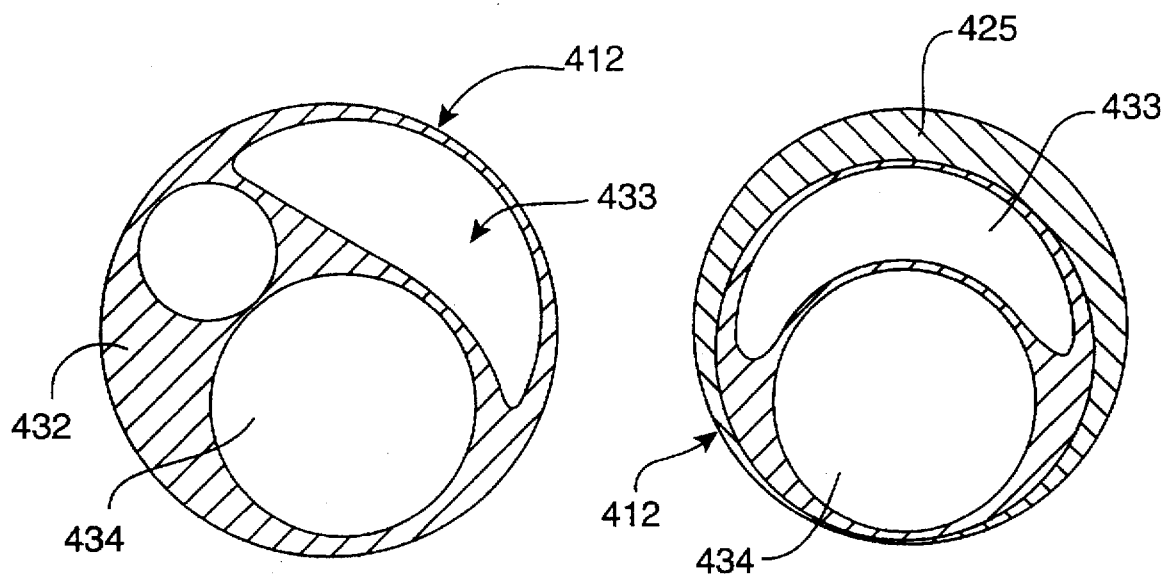
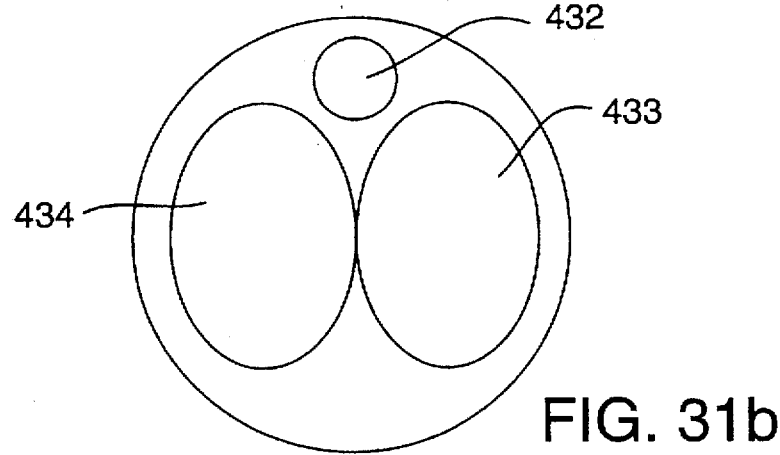

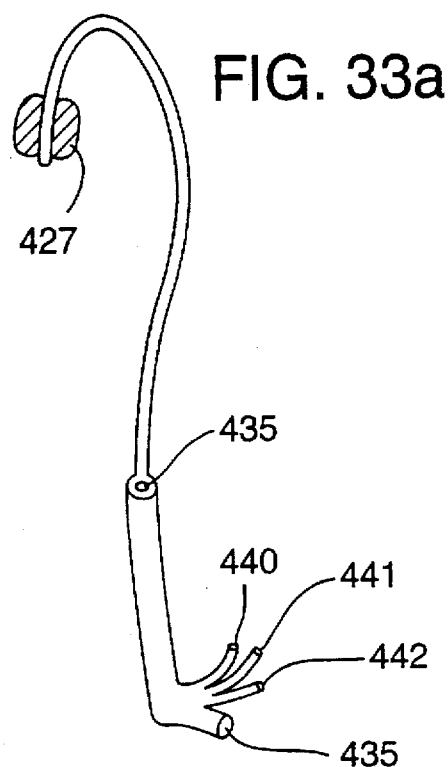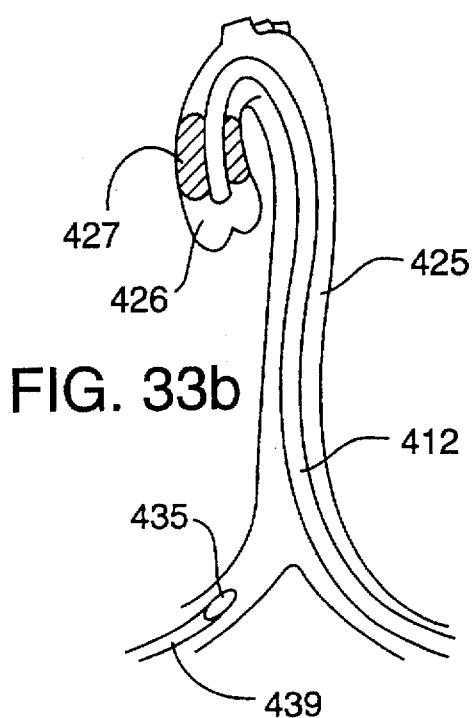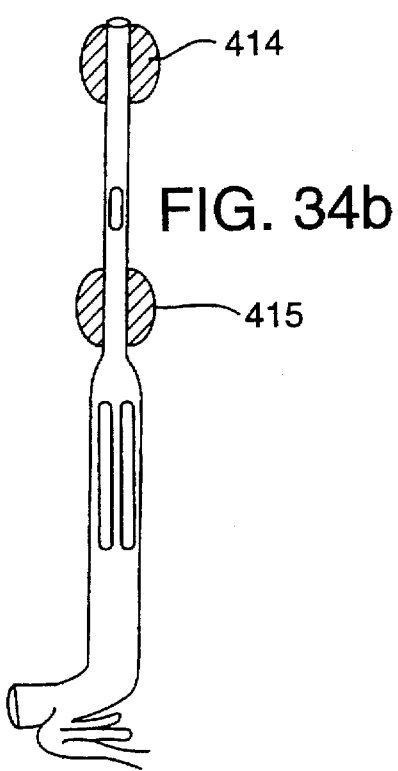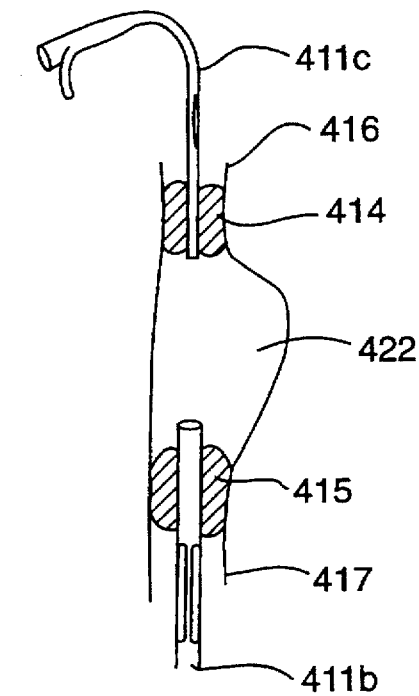

DEVICES AND METHODS FOR INTRACARDIAC PROCEDURES

CROSS-REFERENCE TO RELATED APPLICATIONS

This is a division of application Ser. No. 08/281,962, filed Jul. 28, 1994, which is a continuation-in-part of application Ser. No. 08/163,241, filed Dec. 6, 1993, now U.S. Pat. No. 5,571,215, which is a continuation-in-part of application Ser. No. 08/023,778, filed Feb. 22, 1993, now U.S. Pat. No. 5,452,733. The complete disclosure of all of these applications are hereby incorporated herein by reference.

FIELD OF THE INVENTION

This invention relates generally to instruments and techniques for performing less-invasive surgical procedures, and more specifically, to instruments and techniques for less-invasive surgery within the heart and great vessels.

BACKGROUND OF THE INVENTION

Various types of surgical procedures are currently performed to investigate, diagnose, and treat diseases of the heart and the great vessels of the thorax. Such procedures include repair and replacement of mitral, aortic, and other heart valves, repair of atrial and ventricular septal defects, pulmonary thrombectomy, treatment of aneurysms, electrophysiological mapping and ablation of the myocardium, and other procedures in which interventional devices are introduced into the interior of the heart or a great vessel.

Using current techniques, many of these procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta between the brachiocephalic artery and the coronary ostia. Cardioplegic fluid is then injected into the coronary arteries, either directly into the coronary ostia or through a puncture in the aortic root, so as to arrest cardiac function. In some cases, cardioplegic fluid is injected into the coronary sinus for retrograde perfusion of the myocardium. The patient is placed on cardiopulmonary bypass to maintain peripheral circulation of oxygenated blood.

Of particular interest to the present invention are intracardiac procedures for surgical treatment of heart valves, especially the mitral and aortic valves. According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendonae, reattachment of severed mitral or tricuspid valve chordae tendonae or papillary muscle tissue, and decalcification of valve and annulus tissue. Alternatively, the valve may be replaced, by excising the valve leaflets of the natural valve, and securing a replacement valve in the valve position, usually by suturing the replacement valve to the natural valve annulus. Various types of replacement valves are in current use, including mechanical and biological prostheses, homografts, and allografts, as described in Bodnar and Frater, *Replacement Cardiac Valves* 1–357 (1991), which is incorporated herein by reference. A comprehensive discussion of heart valve diseases and the surgical treatment thereof is found in Kirklin and Barratt-Boyes, *Cardiac Surgery* 323–459 (1986), the complete disclosure of which is incorporated herein by reference.

The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into an anterior position accessible through the sternotomy. An opening, or atriotomy, is then made in the right side of the left atrium, anterior to the right pulmonary veins. The atriotomy is retracted by means of sutures or a retraction device, exposing the mitral valve directly posterior to the atriotomy. One of the forementioned techniques may then be used to repair or replace the valve.

An alternative technique for mitral valve access may be used when a median sternotomy and/or rotational manipulation of the heart are undesirable. In this technique, a large incision is made in the right lateral side of the chest, usually in the region of the fifth intercostal space. One or more ribs may be removed from the patient, and other fibs near the incision are retracted outward to create a large opening into the thoracic cavity. The left atrium is then exposed on the posterior side of the heart, and an atriotomy is formed in the wall of the left atrium, through which the mitral valve may be accessed for repair or replacement.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of a replacement valve through the atriotomy for attachment within the heart. However, these invasive, open-chest procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of current techniques.

What is needed, therefore, are devices and methods for carrying out heart valve repair and replacement as well as other procedures within the heart and great vessels that reduce the trauma, risks, recovery time and pain that accompany current techniques. The devices and methods should facilitate surgical intervention within the heart or great vessels without the need for a gross thoracotomy, preferably through small incisions within intercostal spaces of the rib cage, without cutting, removing, or significantly deflecting the patient's ribs or sternum. In particular, the devices and methods should allow for removal of tissue from the thoracic cavity, as well as for introduction of surgical instruments, visualization devices, replacement valves and the like into the thoracic cavity, to facilitate heart valve repair and replacement. Preferably, the devices and methods should facilitate replacement of a heart valve with various types of prostheses, including mechanical and biological prostheses, homografts, and allografts.

SUMMARY OF THE INVENTION

The invention provides devices and methods for performing less-invasive surgical procedures within an organ or vessel, and particularly, within the heart and great vessels of the thoracic cavity. The devices and methods of the invention facilitate intervention within the heart or great vessels without the need for a median sternotomy or other form of gross thoracotomy, substantially reducing trauma, risk of complication, recovery time, and pain for the patient. Using the devices and methods of the invention, surgical procedures may be performed through percutaneous penetrations within intercostal spaces of the patient's rib cage, without cutting, removing, or significantly displacing any of the patient's ribs or sternum. The devices and methods are particularly well-adapted for heart valve repair and replacement, facilitating visualization within the patient's thoracic cavity, repair or removal of the patient's natural valve, and, if necessary, attachment of a replacement valve in the natural valve position. The invention facilitates valve replacement with any of a variety of commercially-available replacement valves, including mechanical prostheses, bioprostheses, homografts, and allografts.

In a first preferred embodiment, the invention provides a method of closed-chest surgical intervention within an internal cavity of the patient's heart or great vessel. Utilizing the method of the invention, the patient's heart is arrested and cardiopulmonary bypass is established. An internal portion of the patient's chest is viewed by means of a scope extending through a percutaneous intercostal penetration in the patient's chest. A cutting means is introduced through a percutaneous intercostal penetration in the patient's chest, and the cutting means is used to form an internal penetration in a wall of the heart or great vessel. An interventional tool is then introduced through a percutaneous intercostal penetration and through the internal penetration in the heart or great vessel to perform a surgical procedure within the internal cavity under visualization by means of the scope. One or more percutaneous cannulae may be positioned within an intercostal space of the chest wall through which the interventional tool may be introduced into the chest cavity. The surgical procedures which may be performed within the heart or great vessel include repair or replacement of heart valves, repair of atrial and ventricular septal defects, pulmonary thrombectomy, treatment of aneurysms, electrophysiological mapping and ablation of the myocardium, myocardial drilling, correction of congenital defects, coronary artery bypass grafting, and other procedures.

The patient's heart is preferably arrested by occluding the patient's aorta between the patient's coronary arteries and the patient's brachiocephalic artery with an expandable member on a distal end of an endovascular catheter. Cardioplegic fluid is then introduced through a lumen in the catheter into the patient's aorta upstream of the expandable member to arrest cardiac function. Alternatively, or in addition to such antegrade cardioplegic fluid delivery, cardioplegic fluid may be delivered in a retrograde manner by means of a catheter positioned in the coronary sinus of the patient's heart. In an alternative approach, an external cross-clamp may be placed thoracoscopically on the aorta through a small incision or cannula in the patient's chest. Cardioplegic fluid may be delivered through either a thoracoscopically introduced cannula or an endovascular catheter extending into the ascending aorta upstream of the cross-clamp.

In one aspect the present invention consists in a method for inducing cardioplegic arrest of a heart in situ in a patient's body, comprising the steps of:

(a) maintaining systemic circulation with peripheral cardiopulmonary by-pass;

(b) occluding the ascending aorta through a percutaneously placed arterial balloon catheter;

(c) introducing a cardioplegic agent into the coronary circulation; and (d) venting the left side of the heart.

The method according to the present invention may be carried out on humans or other mammalian animals. The method is of particular applicability in humans as it allows an alternative approach to open heart surgery and the development of closed cardioscopic surgery. The method according to the invention enables a percutaneous by-pass system to be associated with cardioplegia, venting and cooling of the heart which subverts the need for median sternotomy. This may, in turn, reduce the complications of the surgery.

The maintenance of the systemic circulation involves establishing a cardiopulmonary by-pass. The blood may be drawn into the by-pass merely by positioning a percutaneous catheter into the right atrium and/or into one or both of the vena cavae through which venous blood may be drawn from the heart into an extracorporeal pump oxygenator. In more preferred embodiments of the invention a single catheter with two inflatable cuffs, or two separate catheters, each with an inflatable cuff are introduced into the vena cavae to occlude them adjacent to their right atrial inlets. This allows isolation of the right atrium and allows blood to be drawn from the vena cavae into the by-pass system. There is also preferably provision for percutaneous communication via one catheter with the right atrium to allow infusion of saline into the right atrium. This infusion has the advantage that it allows the heart to be cooled and improves visual acuity within the right heart allowing direct cardioscopic examination and/or intervention.

The catheter used to decompress the right atrium and to draw blood into the by-pass is preferably introduced through the femoral vein by percutaneous puncture or direct cut down. If other than simple venous drainage is required catheters with inflatable cuffs, as described above, are placed preferably such that in inflatable cuff of the cannula is positioned within each of the inferior (suprahepatic) and superior vena cavae. There is preferably a lumen in the cannula acting as a common blood outlet from the vena cavae leading to the pump oxygenator. A separate lumen is preferably used to infuse saline between the two inflated cuffs into the right atrium. If, alteratively, separate catheters are used to occlude each of the inferior and superior vena cavae than the cannula for the inferior vena cavae is preferably introduced percutaneously from the femoral vein and that for the superior vena cavae is introduced percutaneously through the jugular or subclavian vein.

The ascending aorta is preferably occluded by a balloon catheter introduced percutaneously through the femoral artery. This catheter must carry adjacent its tip an inflatable cuff or balloon of sufficient size that upon being inflated it is able to completely occlude the ascending aorta. The length of the balloon should preferably not be so long as to impede the flow of blood or other solution to the coronary arteries or to the brachiocephalic, left carotid or left subclavian arteries. A balloon length of about 40 mm and diameter of about 35 mm is suitable in humans. The balloon is of a cylindrical shape to fully and evenly accommodate the lumen of the ascending aorta. This maximizes the surface area contact with the aorta, and allows for even distribution of occlusive pressure.

The balloon of the catheter is preferably inflated with a saline solution to avoid the possibility of introducing into the patient an air embolism in the event that the balloon ruptured. The balloon should be inflated to a pressure sufficient to prevent regurgitation of blood into the aortic root and to prevent migration of the balloon into the root whilst not being so high as to cause damage or dilation to the aortic wall. An intermediate pressure of the order of 350 mmHg has been proven effective in trials.

The aortic catheter is preferably introduced under fluoroscopic guidance over a suitable guidewire. Transoesophageal echocardiography can alternatively be used for positioning as has been described with reference to the venous catheter. The catheter may serve a number of separate functions and the number of lumina in the catheter will depend upon how many of those functions the catheter is to serve. The catheter can be used to introduce the cardioplegic agent, normally in solution, into the aortic root via one lumen. The luminal diameter will preferably be such that a flow of the order of 250–500 ml/min of cardioplegic solution can be introduced into the aortic mot under positive pressure to perfuse adequately the heart by way of the coronary arteries. The same lumen can, by applying negative pressure to the lumen from an outside source, effectively vent the left heart of blood or other solutions. It may also be desirable to introduce medical instruments and/or a cardioscope into the heart through another lumen in the catheter. The lumen should be of a diameter suitable to pass a fibre-optic light camera of no greater than 3 mm diameter. It is however, preferable that the diameter and cross-sectional design of the internal lumina is such that the external diameter of the catheter in its entirety is small enough to allow its introduction into the adult femoral artery by either percutaneous puncture or direct cut-down The oxygenated blood returning to the body from the by-pass system may be conveyed into the aorta from another lumen in the cannula carrying the balloon. In this case the returning blood is preferably discarded from the catheter in the external iliac artery. In another embodiment of the invention, and in order to reduce the diameter of the catheter carrying the balloon, a separate arterial catheter of known type may be used to return blood to the patient from the by-pass system. In this case a short catheter is positioned in the other femoral artery to provide systemic arterial blood from the by-pass system. The control end of the catheter, i.e. that end that remains outside of the body, should have separate ports of attachment for the lumina. The catheter length should be approximately 900 mm for use in humans.

The cardioplegic agent may be any of the known materials previously known to be useful, or in the future found to be useful, as cardioplegic agents. The agent is preferably infused as a solution into the aortic root through one of the lumina of the aortic catheter. In another aspect the present invention consists in a catheter for use in occluding the ascending aorta comprising an elongate tube having one or more continuous lumina along its length, an inflatable cuff is disposed about the tube adjacent one end thereof, the cuff being of such a size that upon being inflated it is able to occlude the ascending aorta of a patient.

The invention thus contemplates, at least in its preferred embodiments, the possibility of effective ascending aortic occlusion, cardioplegia, venting, right heart deflation and topical cooling in association with extracorporeal cardiopulmonary by-pass all without necessitating a median sternotomy or other thoracic incision.

The catheter and method used to induce cardioplegic arrest may be used in a number of surgical procedures. These include the following:

(1) Coronary artery revascularization such as:
(a) angioscopic laser introduction or angioscopic balloon angioplasty catheter into the coronary arteries via one lumen of the aortic catheter; or
(b) thoracoscopic dissection of one or both of the mammary arteries with revascularization achieved by distal anastomoses of the internal mammary arteries to coronary arteries via a small left anterior thoracotomy.

(2) Secundum—type atrial septal defect repair such as by:
(a) "Closed" cardioscopic closure, or
(b) Closure as an "open" procedure via a mini-right thoracotomy.

(3) Sinus venosus defect repairs similar to 2 above.

(4) Infundibular stenosis relief by cardioscopic techniques.

(5) Pulmonary valvular stenosis relief by cardioscopic techniques.

(6) Mitral valve surgery via a small right thoracotomy.

(7) Aortic stenosis relief by the introduction of instrumentation via a lumen in the aortic catheter into the aortic root.

(8) Left ventricular aneurysm repair via a small left anterior thoracotomy.

In a preferred embodiment, the surgical procedure comprises surgically treating a heart valve. Such surgical treatment may involve repairing the valve by introducing instruments through an intercostal penetration and through the internal penetration in the heart to perform, for example, annuloplasty, quadrangular resection of valve leaflets, commissurotomy, reattachment of chordae tendonae or papillary muscle tissue, shortening of chordae tendonae, decalcification, and the like.

The heart valve may also be replaced with a replacement valve. In this embodiment, the method may further comprise the step of removing all or part of the patient's natural heart valve by means of a cutting tool introduced through a percutaneous intercostal penetration and through the internal penetration in the heart. The method further comprises the step of introducing a replacement valve through a percutaneous intercostal penetration and through the internal penetration into the internal cavity within the heart. The replacement valve is then fastened within the heart, usually by means of an instrument introduced through a percutaneous intercostal penetration and through the internal penetration in the heart wall.

The method may further include the step of sizing the patient's heart valve before the replacement valve is introduced. In an exemplary embodiment, a sizing instrument is introduced through a percutaneous intercostal penetration and through the internal penetration in the heart to measure the size of the valve annulus and to determine the size of the replacement valve.

The replacement valve may be fastened in position in various ways, including suturing the replacement valve to an annulus at the natural valve position in the heart. In one embodiment, the sutures are applied to the annulus at the valve position, drawn out of the patient's body through the internal penetration and through a percutaneous intercostal penetration, and then applied to the replacement valve. The sutures may further be radially arranged in spaced-apart locations about an organizer ring disposed outside of the patient's body. The sutures are then held in tension as the replacement valve is introduced into the interior of the heart and positioned in the natural valve position. The replacement valve may be introduced by means of a valve holder attached to an elongated handle, or simply pushed along the sutures by means of the surgeon's hands or conventional tools such as forceps or needle drivers.

In a particular preferred embodiment, the heart valve comprises a mitral valve which is disposed between the left atrium and left ventricle of the patient's heart. A percutaneous penetration is made within an intercostal space in a right lateral portion of the patient's chest, usually within the fourth, fifth, or sixth intercostal space. From this penetration, an internal penetration may be formed in the wall of the left atrium at a location which is in a generally straight line drawn from the penetration in the right lateral portion of the chest to the patient's mitral valve. In this way, surgical instruments may be introduced from the penetration in the right chest to form the internal penetration in the heart wall, repair or excise the patient's natural valve, and introduce and attach a replacement valve.

In a further aspect of the invention, a prosthesis assembly is provided for closed-chest replacement of a heart valve. The prosthesis assembly comprises a replacement valve having an annular attachment portion and a movable valve portion coupled to the attachment portion. The prosthesis assembly further includes holder means releasably mounted to the attachment portion, wherein the holder means is configured to allow introduction of the replacement valve through an intercostal space in the patient's chest.

In a preferred embodiment, the replacement valve and the holder means together have a profile with a width which is less than the width of the intercostal space. Preferably, the intercostal space is less than about 20 mm in width. The attachment portion of the replacement valve will usually have an outer diameter which is greater than the intercostal width.

The holder means of the device preferably comprises an elongated handle having a distal end mounted to the replacement valve and a proximal end opposite the distal end. The handle is configured to introduce the replacement valve into the patient's heart through the intercostal space. Preferably, the handle is at least about 20 cm in length to allow positioning the replacement valve in the heart from a right lateral portion of the patient's chest. The handle may further include means for releasing the replacement valve, the releasing means being configured for actuation from the proximal end of the handle.

The handle may also include means for pivoting the replacement valve from a first orientation for introduction through the intercostal space to a second orientation for attachment in the patient's heart. The pivoting means is configured for actuation from a proximal end of the handle. In this way, the replacement valve may be introduced edge-first through the intercostal space, then pivoted about an axis generally perpendicular to the handle into an orientation suitable for attachment within the patient's heart. Alternatively, the valve prosthesis may be collapsible or compressible to permit introduction through an intercostal space into the thoracic cavity.

Preferably, the replacement valve is premounted to the holder means and the two are sterilized and packaged together in a sterile pack. In this way, the pack may be opened in the sterile operating room environment with the valve and holder ready for immediate surgical use.

In a further embodiment, the invention provides a thoracoscopic device for placement of a replacement valve in a valve position of a patient's heart. In a preferred embodiment, the thoracoscopic device comprises an elongated handle configured for positioning through an intercostal space in the patient's chest, as described above. The device includes means at a distal end of the handle for releasably holding a replacement valve in an orientation for introduction through the intercostal space, and may further include means for pivoting the replacement valve relative to the handle from a first orientation for introduction through the intercostal space, to a second orientation for placement in the valve position. The thoracoscopic device further includes, in a preferred embodiment, means at the proximal end of the handle for releasing the replacement valve from the holding means once the prosthesis has been positioned and secured within the heart.

In a further aspect of the invention, a percutaneous access cannula is provided to facilitate closed-chest replacement of a heart valve in a patient's heart. The access cannula comprises a cannula body configured for placement in an intercostal space in the patient's chest, the cannula having a distal end, a proximal end, and a lumen extending therebetween. The lumen is configured to allow passage of a replacement valve therethrough. An obturator is positionable in the lumen to facilitate introduction of the cannula body. The obturator has a cross-sectional width that is equal to or less than the width of the intercostal space, and a cross-sectional height that is greater than the cross-sectional width.

The replacement valve has an annular attachment portion with an outer diameter, and the obturator as well as the lumen in the cannula have a cross-sectional height at least equal to the outer diameter, allowing the replacement valve to be introduced through the lumen of the cannula. In one embodiment, the cross-sectional height of the lumen in the cannula is about two to six times the cross-sectional width. The lumen and obturator may have a rectangular cross-section, oval cross-section, or other shape. The cannula body may be rigid or deformable, while the obturator is usually rigid to facilitate introduction.

The access cannula may further be provided with suture retaining means on its proximal end configured to retain a plurality of sutures in a spaced-apart relationship. The suture retaining means may have various configurations, such as a plurality of slots in a proximal end of the cannula body in circumferentially spaced positions around the lumen. The slots in the access cannula may further include means such as slitted, elastomeric inserts, for frictionally engaging the sutures to maintain tension thereon while the prosthesis is introduced into the heart.

A second organizing ring may also be provided in a position spaced-apart from the access cannula outside of the patient's body. The second organizing ring has an interior passage through which the sutures may extend and a plurality of means circumferentially spaced around the passage for frictionally engaging the sutures. In this way, sutures may be applied to the valve annulus in the patient's heart, drawn through the lumen in the cannula and retained in the suture organizing means on the access cannula's proximal end. The sutures may then be applied to the replacement valve and retained in the second organizing ring. Once all of the sutures have been applied to the prosthesis, the prosthesis may be introduced into the heart by sliding it along the sutures, which are held in tension by the second organizing ring. Alternatively, the sutures may be held in tension by individual clamps, tape, commercially-available suture organizers, or other means for exerting traction on the free ends of each individual suture.

The invention further provides a system for closed-chest replacement of a heart valve in a patient's heart. The system includes means for forming a percutaneous intercostal penetration in the patient's chest, and a visualization scope configured to pass through an intercostal space in the patient's chest for viewing an internal chest cavity. Means are also provided for arresting the patient's heart from a location outside of the chest cavity. A cardiopulmonary bypass system, including means for delivering oxygenated blood to the patient's arterial system, is provided for maintaining peripheral circulation of oxygenated blood. Cutting means positionable through a percutaneous intercostal penetration into the chest cavity are provided for forming an internal penetration in a wall of the patient's heart or great vessel. The system further provides interventional means positionable through a percutaneous intercostal penetration and through the internal penetration for performing a surgical procedure within the heart or great vessel.

In a preferred embodiment, the means for arresting the heart comprises an endovascular catheter having expandable means near its distal end for occluding the patient's ascending aorta between the patient's coronary arteries and the patient's brachiocephalic artery. The catheter further includes an internal lumen for delivering cardioplegic fluid into the aorta upstream of the expandable means to perfuse the myocardium through the coronary arteries.

The interventional means preferably comprises means for securing a replacement valve in a valve position within the patient's heart. Usually, the replacement valve securing means comprises an elongated handle like that described above, having means at its distal end for releasably holding a replacement valve. The handle may also facilitate pivoting the replacement valve for introduction through an intercostal space.

Preferably, the system also includes at least one cannula positionable in a percutaneous intercostal penetration, through which surgical instruments or a replacement valve may be introduced into the thoracic cavity. The cannula may have a lumen with a cross-sectional height greater than its width to allow edge-first introduction of a replacement valve that has an outer diameter larger than the intercostal space, as described above.

The system may further include cutting means positionable through a percutaneous intercostal penetration and through the internal penetration in the patient's heart for removing at least a portion of the patient's heart valve. The cutting means for removing the heart valve may comprise scissors, retractable knife, biters, or the like.

The system preferably includes means positionable through a percutaneous intercostal penetration and through the internal penetration for sizing an annulus of the patient's heart valve. In one embodiment, the sizing means comprises an elongated shaft and a plurality of interchangeable sizing disks of various sizes attachable to a distal end of the shaft. The shaft and sizing disk may be introduced through a percutaneous intercostal penetration and through the internal penetration to position the sizing disk adjacent to the annulus of the patient's heart valve, allowing a comparison of the annulus diameter to the disk diameter. The sizing disk may be pivotable relative to the shaft to allow introduction into the thoracic cavity through an intercostal space. Alternative means for sizing may also be used, such as expandable baskets, balloons, endoscopic or endovascular visualization, fluoroscopy, or transesophageal echocardiography.

The system may further include means for attaching the replacement valve to the patient's heart, which comprises, in one embodiment, means for suturing the replacement valve to a valve annulus in the patient's heart. The system preferably includes organizing means for maintaining the sutures in spaced-apart positions outside of the chest cavity after the sutures have been applied to the valve annulus within the heart. The organizing means is preferably fixed to a proximal end of a cannula disposed in a percutaneous intercostal penetration, as described above. In this way, the sutures may be applied to the natural valve annulus within the patient's heart, drawn out of the chest cavity through the cannula lumen, and positioned in spaced-apart positions about the circumference of the proximal end of the cannula. Means may also be provided for maintaining tension on the ends of the sutures after they have been applied to the replacement valve. This facilitates advancing the replacement valve along the sutures, through the lumen in the cannula, and into the chest cavity.

The system may further include retraction means positionable through an intercostal space in the patient's chest for opening the internal penetration in the wall of the heart or great vessel. The retraction means may comprise a collapsible rake, tethered clamp, retraction sutures, or the like.

A further understanding of the nature and advantages of the invention may be realized by reference to the remaining portions of the specification and the drawings.

BRIEF DESCRIPTION OF THE DRAWINGS

FIG. 12A is a side view of angled scissors in the system of FIG. 1.

FIGS. 12B–12D are side views of a distal portion of the scissors of FIG. 12A showing alternative embodiments thereof.

FIG. 13 is a side view of a retractable knife in the system of FIG. 1.

FIGS. 14A–14B are side and top views, respectively, of grasping forceps in the system of FIG. 1.

FIGS. 16A–16B are side and top views, respectively, of needle drivers in the system of FIG. 1.

FIG. 19A is a side view of the prosthesis introducer of FIG. 18.

FIGS. 19B–19C are bottom and side views, respectively, of a distal portion of the prosthesis introducer of FIG. 18.

FIGS. 19D–19E are top and side views, respectively, of a stationary arm of the prosthesis introducer of FIG. 18.

FIGS. 19F–19G are top and side views, respectively, of a movable arm of the prosthesis introducer of FIG. 18.

FIG. 20A is a side partial cut-away view of the prosthesis introducer of FIG. 18.

FIG. 20B is a top partial cut-away view of a distal portion of the prosthesis introducer of FIG. 18.

FIGS. 22, 23A and 23B are top and side views, respectively, of the sizing disk of FIG. 21.

FIGS. 23A–23B are top and side views, respectively, of the sizing disk of FIG. 21.

FIGS. 24A–24C are front, top, and side views, respectively of a suture organizing ring in the system of FIG. 1.

FIGS. 25A–25B are side and top views, respectively of a knot-pushing device in the system of FIG. 1.

FIG. 30 is a partly cut away side elevational view of the balloon end of the catheter of FIG. 29 in an inflated condition;

FIG. 31a is a cross-sectional view of the catheter of FIG. 29 intermediate the control end and the balloon end;

FIG. 31b is an alternative cross-sectional arrangement of the lumina in the catheter of FIG. 29;

FIG. 32 is a cross-sectional view through the balloon end of the catheter of FIG. 29;

FIGS. 33a and 33b show schematically two alternative arrangements to the catheter shown in FIG. 29;

FIGS. 34a and 34b show schematically two alternative catheter arrangements for the isolation of the right atrium and venous drainage.

DETAILED DESCRIPTION OF SPECIFIC EMBODIMENTS

The invention provides methods and devices for performing surgical interventions within the heart or a great vessel such as the aorta, superior vena cava, inferior vena cava, pulmonary artery, pulmonary vein, coronary arteries, and coronary veins, among other vessels. While the specific embodiments of the invention described herein will refer to mitral valve repair and replacement, it should be understood that the invention will be useful in performing a great variety of surgical procedures, including repair and replacement of aortic, tricuspid, or pulmonary valves, repair of atrial and ventricular septal defects, pulmonary thrombectomy, removal of atrial myxoma, patent foramen ovale closure, treatment of aneurysms, electrophysiological mapping and ablation of the myocardium, myocardial drilling, coronary artery bypass grafting, angioplasty, atherectomy, correction of congenital defects, and other procedures in which interventional devices are introduced into the interior of the heart, coronary arteries, or great vessels. Advantageously, the invention facilitates the performance of such procedures through percutaneous penetrations within intercostal spaces of the rib cage, obviating the need for a median sternotomy or other form of gross thoracotomy.

The terms "percutaneous intercostal penetration" and "intercostal penetration" as used herein refer to a penetration, in the form or a small cut, incision, hole, cannula, trocar sleeve, or the like, through the chest wall between two adjacent ribs, wherein the patient's rib cage and sternum remain substantially intact, without cutting, removing, or significantly displacing the ribs or sternum. These terms are intended to distinguish a gross thoracotomy such as a median sternotomy, wherein the sternum and/or one or more ribs are cut or removed from the rib cage, or one or more ribs are retracted significantly, to create a large opening into the thoracic cavity. A "percutaneous intercostal penetration" may abut or overlap the adjacent ribs between which it is formed, but the maximum width of the penetration which is available for introduction of instruments, prostheses and the like into the thoracic cavity will be the width of the intercostal space, bounded by two adjacent ribs in their natural, substantially undeflected positions. It should be understood that one or more ribs may be retracted or deflected a small amount without departing from the scope of the invention; however, the invention specifically seeks to avoid the pain, trauma, and complications which result from the large deflection or cutting of the ribs in conventional, open-chest techniques.

Figure 1:
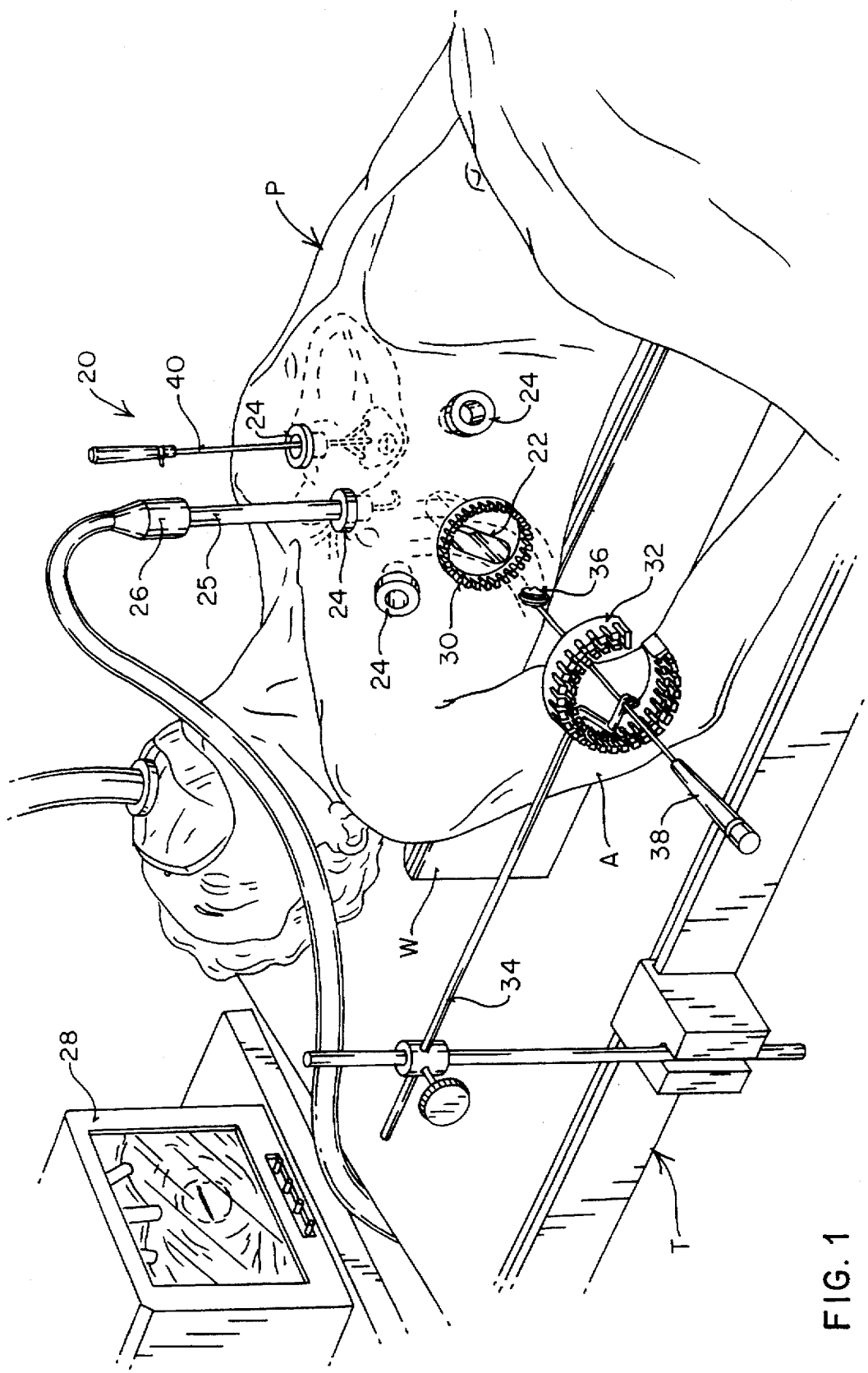
FIG. 1 is a perspective view of a system for closed-chest mitral valve replacement constructed in accordance with the principles of the present invention, showing the use of the system in a patient.

A first preferred embodiment of a system and method of closed-chest mitral valve replacement according to the invention will be described with reference to FIGS. 1–10. FIG. 1 illustrates a system 20 for closed-chest valve replacement positioned in a patient P on an operating table T. Preferably, a wedge or block W having a top surface angled at approximately 20° to 45° is positioned under the right side of patient P so that the right side of the patient's body is somewhat higher than the left side. The patient's right arm A is allowed to rotate downward to rest on table T, exposing the right lateral side of the patient's chest.

The valve replacement system 20 includes an access cannula 22 positioned percutaneously within an intercostal space between two ribs (shown in phantom) in a right lateral side of the patient's chest. Additional thoracoscopic trocar sleeves 24 of conventional construction are positioned within intercostal spaces in the right lateral chest inferior and superior to access cannula 22, as well as in the right anterior (or ventral) portion of the chest. An endoscope 25 of conventional construction is positioned through a percutaneous intercostal penetration into the patient's chest, usually through one of trocar sleeves 24. The distal end of endoscope 25 (shown in phantom) is preferably configured to view at an angle between about 30° and 90° relative to the shaft of endoscope 25, to facilitate visualization of the heart from the right portion of the thoracic cavity. A light source (not shown) is also provided on endoscope 25 to illuminate the thoracic cavity. A video camera 26 is mounted to the proximal end of endoscope 25, and is connected to a video monitor 28 for viewing the interior of the thoracic cavity. A first suture organizing ring 30 is mounted to a proximal end of access cannula 22. A second organizing ring 32 is mounted to a support stand 34 fixed to table T. A replacement valve 36 is held at the distal end of an introducer 38 between first organizing ring 30 and second organizing ring 32. Introducer 38 extends through second organizing ring 32 and is supported by support stand 34. Additional instruments to be used in a procedure such as a retractor 40, as well as cutting, suturing, stapling, aspirating, irrigating and other devices, may be introduced through access cannula 22, trocar sleeves 24, and/or small, percutaneous incisions within intercostal spaces of the rib cage.

Figure 2:
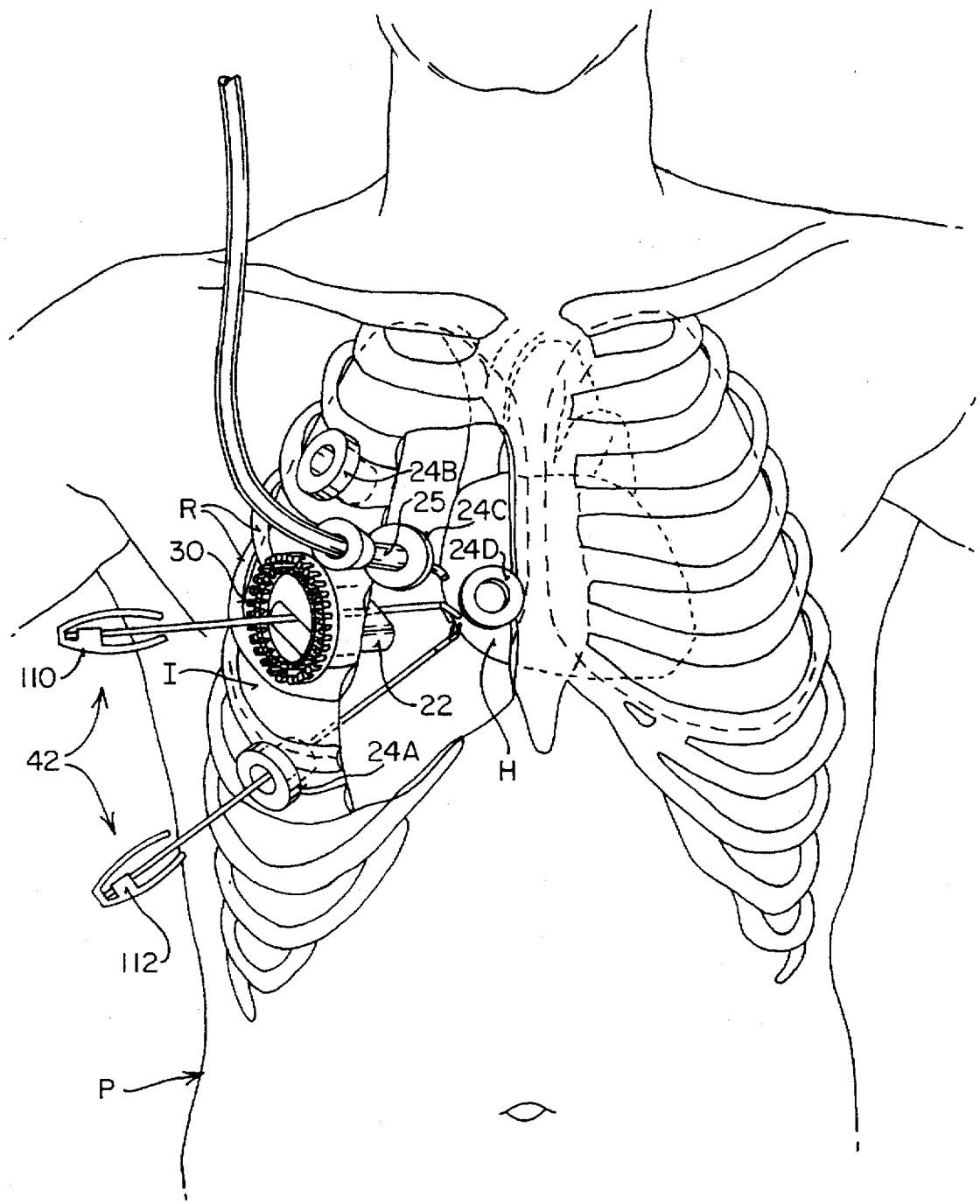
FIG. 2 is a front view of the system of FIG. 1, showing the positioning of the system in the patient's chest.

Referring now to FIG. 2, access cannula 22 is positioned within an intercostal space I in the right lateral side of the chest, preferably in the third, fourth, fifth, or sixth intercostal space between adjacent ribs R. Additional trocar sleeves 24A, 24B are positioned within intercostal spaces superior and inferior to access cannula 22 in the right lateral side of the chest. Access cannula 22 and trocar sleeves 24A, 24B are positioned so that instruments 42 introduced through them may be directed toward the right side of the left atrium of the heart H. A trocar sleeve 24C is positioned in an intercostal space in the right anterior side of the chest such that endoscope 25 may be introduced to view the thoracic cavity and heart H without interfering with instruments introduced through access cannula 22 or trocar sleeves 24A, 24B. An additional trocar sleeve 24D is positioned in an intercostal space in the anterior side of the chest just to the right of the sternum and anterior to the right lateral side of the heart H.

It will be understood to those of ordinary skill in the art that, in some cases, it may desirable to eliminate some or all of trocar sleeves 24 and/or access cannula 22, and introduce instruments directly through small, percutaneous intercostal incisions in the chest. Advantageously, unlike laparoscopic, arthroscopic, and other endoscopic procedures, no distension of the chest is required using the method of the invention, so that leakage of distension fluid through percutaneous penetrations is not of concern. Thus, either thoracoscopic trocar sleeves without fluid seals or percutaneous incisions may be utilized for instrument introduction into the thoracic cavity. Trocar sleeves are generally preferred, however, in order to provide an open passage into the thoracic cavity, to protect adjacent tissue from injury resulting from contact with instruments, and to avoid damaging instruments, endoscopes, replacement valves, and the like when introduced into the thoracic cavity.

Referring now to FIGS. 11A–11D, access cannula 22 will be described in greater detail. Access cannula 22 comprises a body 44 having a proximal end 46, a distal end 48, and a passage 50 extending therebetween. Body 44 is configured to fit within an intercostal space I without significant deflection of adjacent ribs R, usually having a width of less than about 20 mm. Passage 50 is configured to facilitate passage of replacement valve 36 therethrough. Replacement valve 36 may have a variety of configurations, but must have a diameter at least equal to that of the patient's natural heart valve, a diameter which commonly exceeds the width of the intercostal spaces in the rib cage. Therefore, in order to avoid cutting or retracting the patient's ribs, replacement valve 36 is introduced edge-first through passage 50 of access cannula 22, as described more fully below. To accommodate such introduction of replacement valve 36, passage 50 usually has a cross-sectional width w of about 12 mm to 20 mm, and a cross-sectional height h that is somewhat greater than cross-sectional width w, usually 2–6 times cross-sectional width w, and preferably in the range of 25 mm to 50 mm. Passage 50 may have various cross-sectional shapes, including oval, rectangular, race-track, and the like. This accommodates a variety of replacement heart valves, including mechanical and biological prostheses, as well as homograft and allograft tissue valves. It will be understood, however, that certain replacement valves may be collapsible or sufficiently small in size so that passage 50 in access cannula 22 may have a round or square cross-section and still allow passage of the replacement valve therethrough. However, a cross-sectional shape in which the height is greater than the width may still be advantageous to allow greater freedom of movement in manipulating the replacement valve and other instruments introduced through passage 50.

Figure 11D:
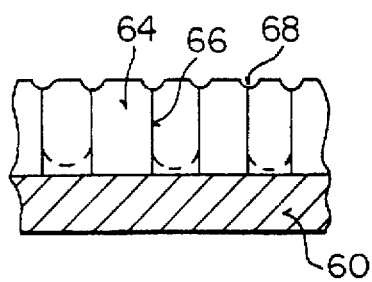
FIG. 11D is a partial cut-away view taken along line 11D—11D in FIG. 11C.
Figure 11C:
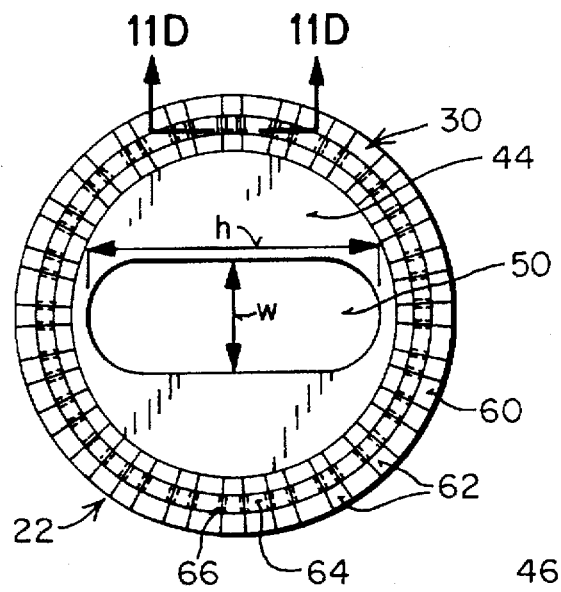
FIGS. 11A–11C are perspective, front, and top views respectively of the access cannula in the system of FIG. 1.
Figure 11B:
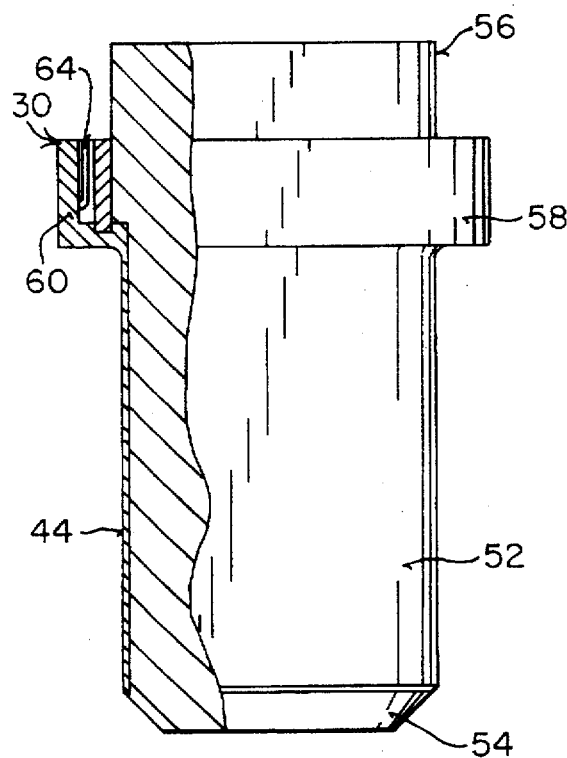
Figure 11A:
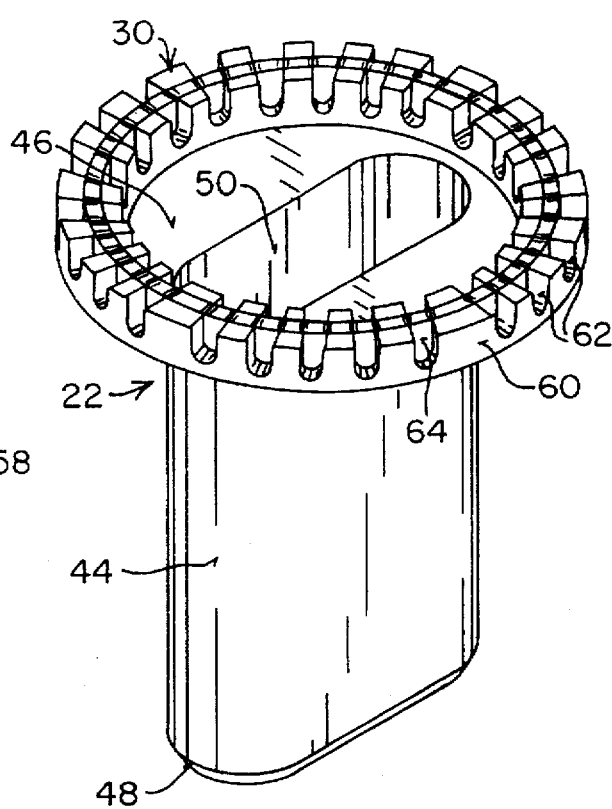

As shown in FIG. 11B, an obturator 52 is positionable in passage 50 to facilitate introduction of access cannula 22 through the chest wall. Obturator 52 has a tapered distal end 54, a proximal end 56, and a rim 58 near proximal end 56 for engaging proximal end 46 of cannula body 44. Usually, obturator 52 is positioned in passage 50 of access cannula 22, and the two are introduced through a small incision formed in an intercostal space in the chest wall. Obturator 52 is then removed from passage 50.

As described briefly above, access cannula 22 may further include a suture organizing ring 30 mounted to its proximal end 46. Suture organizing ring 30 has a ring-shaped body 60 and a plurality of slots 62 circumferentially spaced about body 60. Usually, between 16 and 32 of slots 62 are provided, depending upon the type of replacement valve and suturing technique to be utilized in the procedure. An elastomeric retaining ring 64 is disposed in a circumferential channel in ring body 60, and has a plurality of slits 66, best seen in FIG. 11D, aligned with each slot 62. Slits 66 are provided with chamfers 68 along the top surface of retaining ring 64 to facilitate positioning sutures within slits 66 for retention therein. The function of suture organizing ring 30 will be described in greater detail below.

Referring again to FIG. 2, once access cannula 22 and trocar sleeves 24 have been positioned in the patient's chest, endoscope 25 is introduced through trocar sleeve 24D and camera 26 is connected to video monitor 28 (FIG. 1). Endoscope 25 is manipulated so as to provide a view of the right side of the heart, and particularly, a right side view of the left atrium. Usually, an endoscope of the type having an articulated distal end, or a distal end disposed at an angle between 30° and 90° will be used, which is commercially available from, for example, Olympus Corp., Medical Instruments Division, Lake Success, N.Y.

At this point in the procedure, if not previously accomplished, the patient is placed on cardiopulmonary bypass (CPB), the patient's right lung is at least partially collapsed, and the patient's heart is arrested. Suitable techniques for arresting cardiac function and establishing CPB without a thoracotomy are described in commonly-assigned, copending applications Ser. No. 07/991,188, filed Dec. 15, 1992, now abandoned, Ser. No. 08/123,411, filed Sep. 17, 1993, now abandoned Ser. No. 08/159,815, filed Nov. 30, 1993, now U.S. Pat. No. 5,433,700 Ser. No. 08/162,742, filed Dec. 3, 1993, now abandoned, and Ser. No. 08/310,818, entitled "System for Cardiac Procedures," now abandoned, all of which are incorporated herein by reference.

Figure 3:
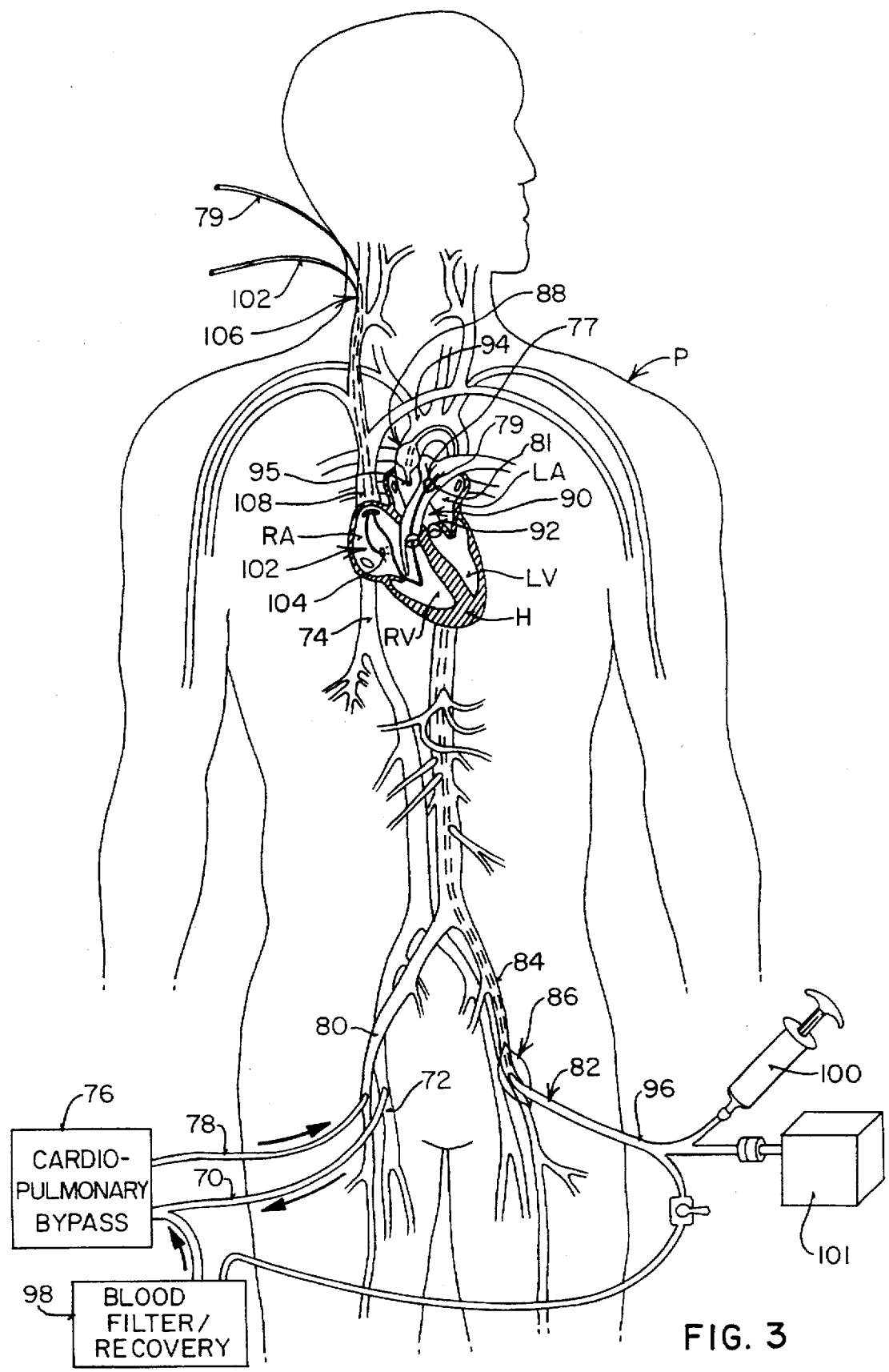
FIG. 3 is a front view of a patient's cardiovascular system illustrating the positioning of a system for arresting the heart and establishing cardiopulmonary bypass in accordance with the principles of the present invention.

As illustrated in FIG. 3, CPB is established by introducing a venous cannula 70 into a femoral vein 72 in patient P and advancing venous cannula 72 into the inferior vena cava 74 and/or into the interior of heart H to withdraw deoxygenated blood therefrom. Venous cannula 70 is connected to a cardiopulmonary bypass system 76 which receives the withdrawn blood, oxygenates the blood, and returns the oxygenated blood to an arterial return cannula 78 positioned in a femoral artery 80.

A pulmonary venting catheter 79 may also be utilized to withdraw blood from the pulmonary trunk 77. Pulmonary venting catheter 79 may be introduced from the neck through the interior jugular vein 106 or a subclavian vein and through superior vena cava 108, or from the groin through femoral vein 72 and inferior vena cava 74. Usually, a Swan-Ganz catheter (not shown) is first introduced and positioned in pulmonary artery 77 using well-known techniques, and pulmonary venting catheter 79 is then introduced over the Swan-Ganz catheter. Blood is withdrawn from pulmonary trunk 77 through a port at the distal end of pulmonary venting catheter 79 and an inner lumen extending through the catheter outside of the patient's body. Pulmonary venting catheter 79 may further have one or more balloons 81 at its distal end proximal to the distal port for occluding pulmonary trunk 77.

An alternative method of venting blood from pulmonary trunk 77 is described in U.S. Pat. No. 4,889,137, which is incorporated herein by reference. In the technique described therein, a catheter is positioned from the interior jugular vein in the neck through the right atrium, right ventricle, and pulmonary valve into the pulmonary artery 77. The catheter has a coil about its periphery which holds the pulmonary valve open so as to drain blood from pulmonary trunk 77, thereby decompressing the left side of the heart.

For purposes of arresting cardiac function, an aortic occlusion catheter 82 is positioned in a femoral artery 84 by a percutaneous technique such as the Seldinger technique, or through a surgical cut-down 86. The aortic occlusion catheter 82 is advanced, usually over a guidewire (not shown), until an occlusion balloon 88 at its distal end is disposed in the ascending aorta 90 between the coronary ostia 92 and the brachiocephalic artery 94. Blood may be vented from ascending aorta 90 through a port 95 at the distal end of the aortic occlusion catheter 82 in communication with an inner lumen in aortic occlusion catheter 82, through which blood may flow to proximal end 96 of catheter 82. The blood may then be directed to a blood filter/recovery system 98 to remove emboli, and then returned to the patient's arterial system via CPB system 76.

When it is desired to arrest cardiac function, occlusion balloon 88 is inflated by injecting inflation fluid, usually a mixture of saline and a radiographic contrast agent, from a syringe 100 connected to proximal end 96 of catheter 82, through an inflation lumen in catheter 82 to the interior of occlusion balloon 88. Occlusion balloon 88 is expanded until it completely occludes ascending aorta 92, blocking blood flow therethrough. A cardioplegic fluid such as potassium chloride (KCl) is then delivered to the myocardium in one or both of two ways. Cardioplegic fluid may be delivered in an anterograde manner from a cardioplegia pump 101 through an inner lumen in aortic occlusion catheter 82 and a port distal to occlusion balloon 88 into the ascending aorta upstream of occlusion balloon 88. Pressure in the aortic root is measured by a pressure measurement device 103 in communication with a pressure lumen in catheter 82 having an opening distal to occlusion balloon 88. The cardioplegic fluid is then infused into the coronary arteries and paralyzes the myocardium.

Alternatively, or in conjunction with such anterograde delivery, cardioplegic fluid may be delivered in a retrograde manner through a retroperfusion catheter 102 positioned in the coronary sinus 104. Retroperfusion catheter 102 may be positioned, usually over a guidewire (not shown), from the neck through the interior jugular vein 106 and superior vena cava 108, or from the groin through a femoral vein 72 and the inferior vena cava 74. Retroperfusion catheter 102 may have one or more balloons (not shown) at its distal end to enhance positioning and infusion of cardioplegia into the coronary sinus. Cardioplegic fluid may thus be infused through the coronary veins into the capillary beds, paralyzing the myocardium.

In a preferred embodiment, the cardioplegic fluid consists of an aqueous KCl solution mixed with oxygenated blood at a ratio of four parts blood to one part KCl solution. The aqueous KCl solution consists of crystalloid KCl mixed with saline to have a concentration in the range of 10–50 mEq K$^+$/liter, preferably 15–30 mEq K$^+$/liter. A cooler such as an ice bath (not shown) is used to cool the cardioplegic fluid to e.g. 3° C.–10° C., so as to maintain the heart at a low temperature and to minimize demand for oxygen. This is usually accomplished without applying external cooling to the heart as is generally applied in conventional open cardiac procedures. The cardioplegic fluid is infused into the ascending aorta through an opening at the distal end of occlusion catheter 82 to maintain a pressure in the aortic root distal to the occlusion balloon sufficient to induce flow of fluid into the coronary arteries through the coronary ostia. A pressure of about 60–80 mmHg as measured through a pressure lumen in catheter 82 is usually sufficient. Cardioplegic fluid is preferably delivered at a flowrate of about 250–350 ml/min. so as to deliver a total volume of 750–1000 ml in about 2–4 minutes, although this may vary depending upon patient anatomy, physiological changes such as coronary dilation, and other factors. In pumping the cardioplegic fluid through the lumen in catheter 82, the fluid should be subject to a pump pressure of no more than about 300 mmHg to minimize damage to the blood component of the mixture. Heart contractions will then cease, with circulation to the remainder of the patient's body maintained by the CPB system. Cardioplegic fluid flow to the patient's myocardium is maintained on a periodic basis, e.g., about every 10–20 minutes for 2–4 minutes, so long as the myocardium is to remain paralyzed. A comprehensive description of cardioplegic techniques suitable for use in the method of the invention is found in Buckberg, *Strategies and logic of cardioplegic delivery to prevent, avoid, and reverse ischemic*

*and reperfusion damage*, J. Thorac. Cardiovasc. Surg. 1987;93: 127–39.

In addition to or instead of infusion of the blood/crystalloid cardioplegic solution, other techniques may be used to arrest heart contractions. A more concentrated crystalloid KCl solution not mixed with blood may be delivered through a lumen in occlusion catheter 82 at higher pressures than with a blood cardioplegic fluid mixture, since without blood in the solution, there is no risk of hemolysis. This allows the inner lumen (as well as the overall catheter shaft) to be of smaller cross-sectional area while still providing the necessary flowrate of fluid into the aortic root. However, the above blood cardioplegia technique is presently preferred because it is generally believed to provide greater myocardial protection. In another alternative technique, the patient's body may be cooled in a cold-temperature environment or by application of cold-packs to the chest to reduce the temperature of the myocardium sufficiently to induce fibrillation. The myocardium may be cooled directly by infusion of cold fluid such as cold blood or saline through the coronary arteries. Alternatively, electrical fibrillation may be accomplished by delivering electrical signals to the myocardium by means of electrodes placed on the exterior surface of the heart or externally on the chest. However, cardiac arrest by means of fibrillation is generally less desirable than chemical cardioplegic paralysis because there remains some degree of heart motion which could make surgical intervention more difficult and because there is a significantly higher demand for oxygen, reducing the safety and duration of the procedure.

The right lung may be collapsed using known techniques. Usually, a tube is introduced through the trachea into the right main stem bronchus, and a vacuum is applied through the tube to collapse the lung.

Periodically during the procedure, it may be necessary to decompress the left side of the heart by removing blood and other fluids which have accumulated in the aortic root, left atrium and/or left ventricle and which have not been removed by the pulmonary artery venting catheter (if utilized). To remove such fluids, suction may be applied through an inner lumen in occlusion catheter 82 so as to aspirate fluids from the aorta, left ventricle, and or left atrium upstream of occlusion balloon 88. Aortic root pressure may be monitored by pressure measurement device 103 via a separate lumen in catheter 82. Such venting is usually performed after each periodic infusion of cardioplegic fluid and additionally as necessary to maintain decompression of the left side of the heart. In some cases, venting through occlusion catheter 82 may be sufficient to maintain left heart decompression throughout the procedure, eliminating the need for a pulmonary artery venting catheter.

Figure 26:
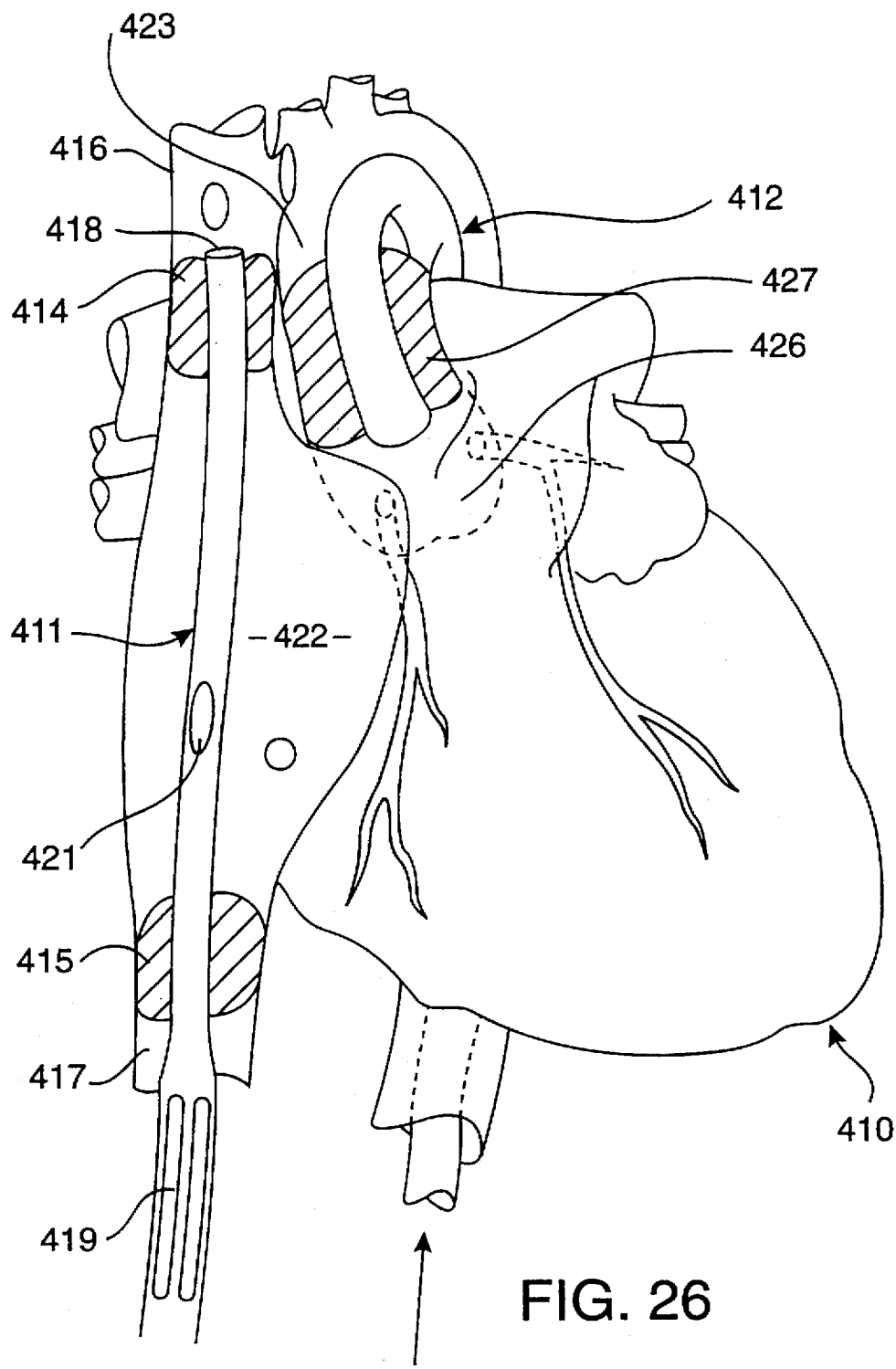
FIG. 26 is a schematic partly cut-away representation of a patient's heart having percutaneous catheters placed therein for carrying out the method according to the present invention.
Figure 27:
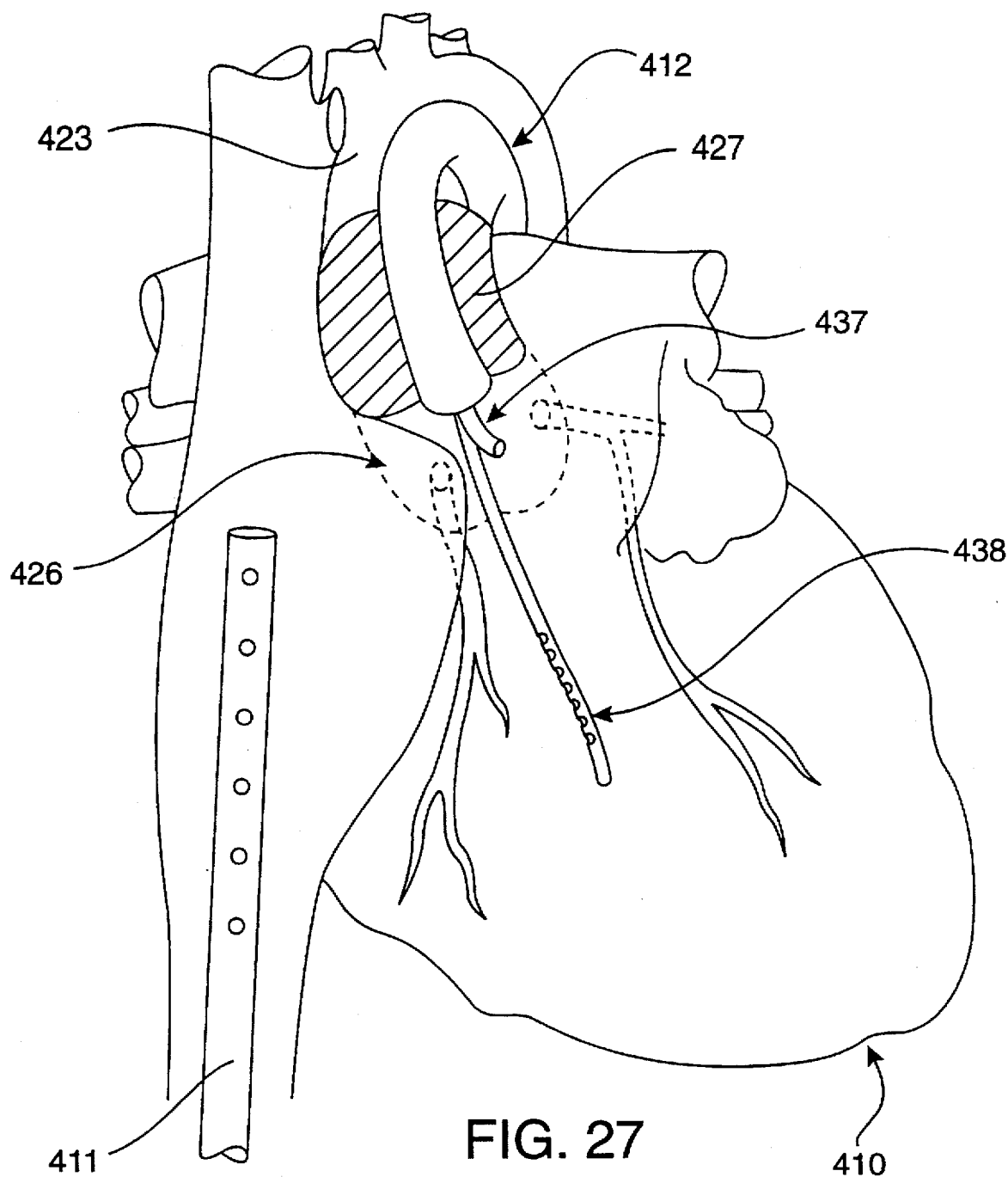
FIG. 27 is a similar view to FIG. 26 showing the aortic catheter in position but including an angioscope and a left ventricular venting cannula introduced into the aortic root and left ventricle respectively, via separate lumina within the aortic catheter.

Additional exemplary embodiments of an endovascular aortic partitioning system according to the invention are illustrated in FIGS. 26–34. The heart 410 of FIGS. 26 and 27 is positioned in the living body of a patient and is accessed percutaneously.

In order to induce cardioplegia in the heart while maintaining the patient it is necessary to divert the patient's blood circulation through an extracorporeal cardiopulmonary by-pass system. This is achieved by isolating the heart 410 on both the venous and arterial sides using appropriate percutaneously inserted venous catheter 411, aortic balloon catheter 412, and if this catheter 412 doesn't have provision for arterial blood return, arterial catheter 439 (see FIG. 28). The venous outflow and arterial inflow lumina of the catheters 411 and 412 of the by-pass system are of sufficient cross sectional area to achieve standard blood flows to maintain the patient's systemic circulation during the period of extracorporeal circulation.

In the case of the use of a single venous double-ballooned catheter 411, as is shown in FIG. 26, the catheter 411 is inserted through the femoral vein preferably. A suitable guide wire is initially inserted and the catheter 411 is then introduced in known manner under fluoroscopic guidance. The catheter 411 includes a pair of separately inflatable balloons 414 and 415 each connected to a balloon inflation control device (not shown) through suitable lumina in the catheter 411. The balloon 414 is adapted to occlude the superior vena cavae 416 while the balloon 415 is adapted to occlude the suprahepatic inferior vena cavae 417. A blood withdrawal lumen in the catheter 411 has an inlet orifice 418 flush with the balloon 414, to avoid venous collapse during blood flow into the catheter 411, and a series of inlet slots 419 in the inferior vena cavae. Blood drawn into the inlets 418 and 419 enters a common single lumen. Blood drawn into the by-pass system through the catheter 411 is oxygenated and returned to the patient in a manner which will be hereinafter described.

A separate lumen in the catheter 411 opens into the right atrium 422 through aperture 421 to allow evacuation of blood from the right heart and the infusion of saline to induce topical cooling and/or to improve visual acuity within the right heart.

In use, after the catheter 411 has been positioned the balloons may be inflated or deflated to vary the rate of venous return to the right atrium 422 and therefore the degree of decompression of the left heart. Venous drainage may be effected by gravitational drainage or by applying a degree of negative pressure to assist flow into the pump oxygenator. It will be appreciated that the distance between the balloons 414 and 415 will need to be correct for a given patient and this may be assessed by X-ray examination to allow selection of an appropriately sized catheter. Alternatively separate catheters 411b and 411c could be used, as is shown in FIG. 34a, for the inferior and superior vena cavae, the cannula 411b being introduced as has been described above and the cannula 411c being introduced through the jugular or subclavian vein. It will also be appreciated that for simple operations not requiring complete occlusion of the right atrium it is possible to merely insert a simple catheter 411 into the tight atrium to draw blood into the by-pass system as is seen in FIG. 27. Positioning under fluoroscopic guidance is not essential in this case.

Figure 28:
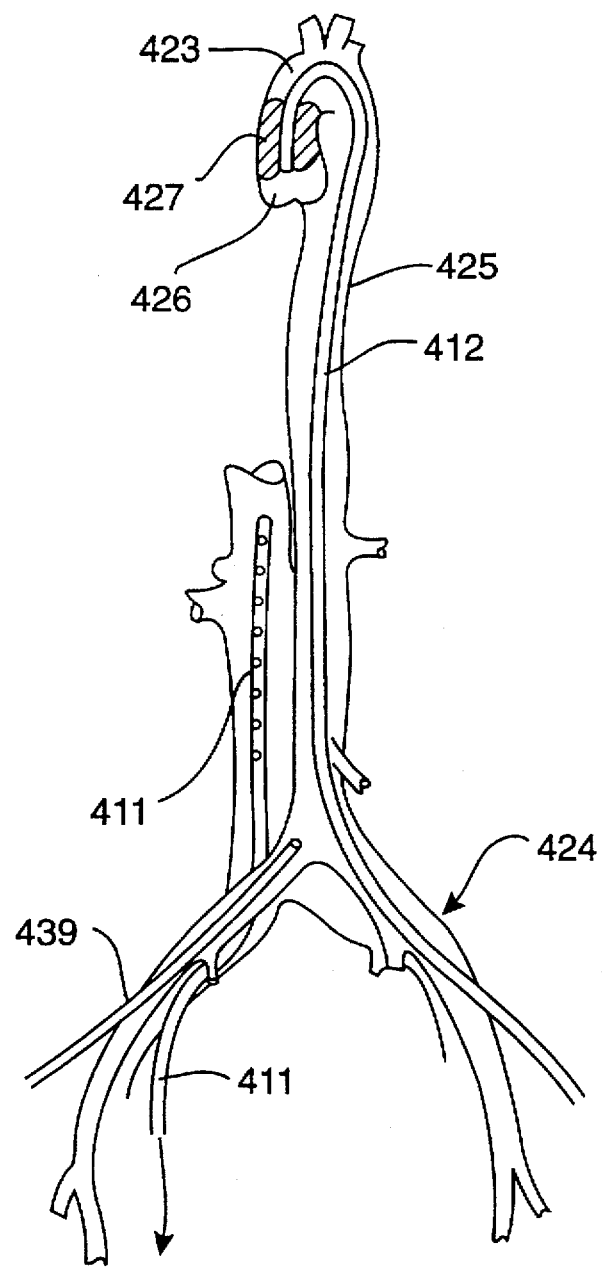
FIG. 28 is a front elevational view of part of the vascular system of a patient showing, inter alia, the aortic balloon catheter positioned in the ascending aorta via the femoral artery.
Figure 29:
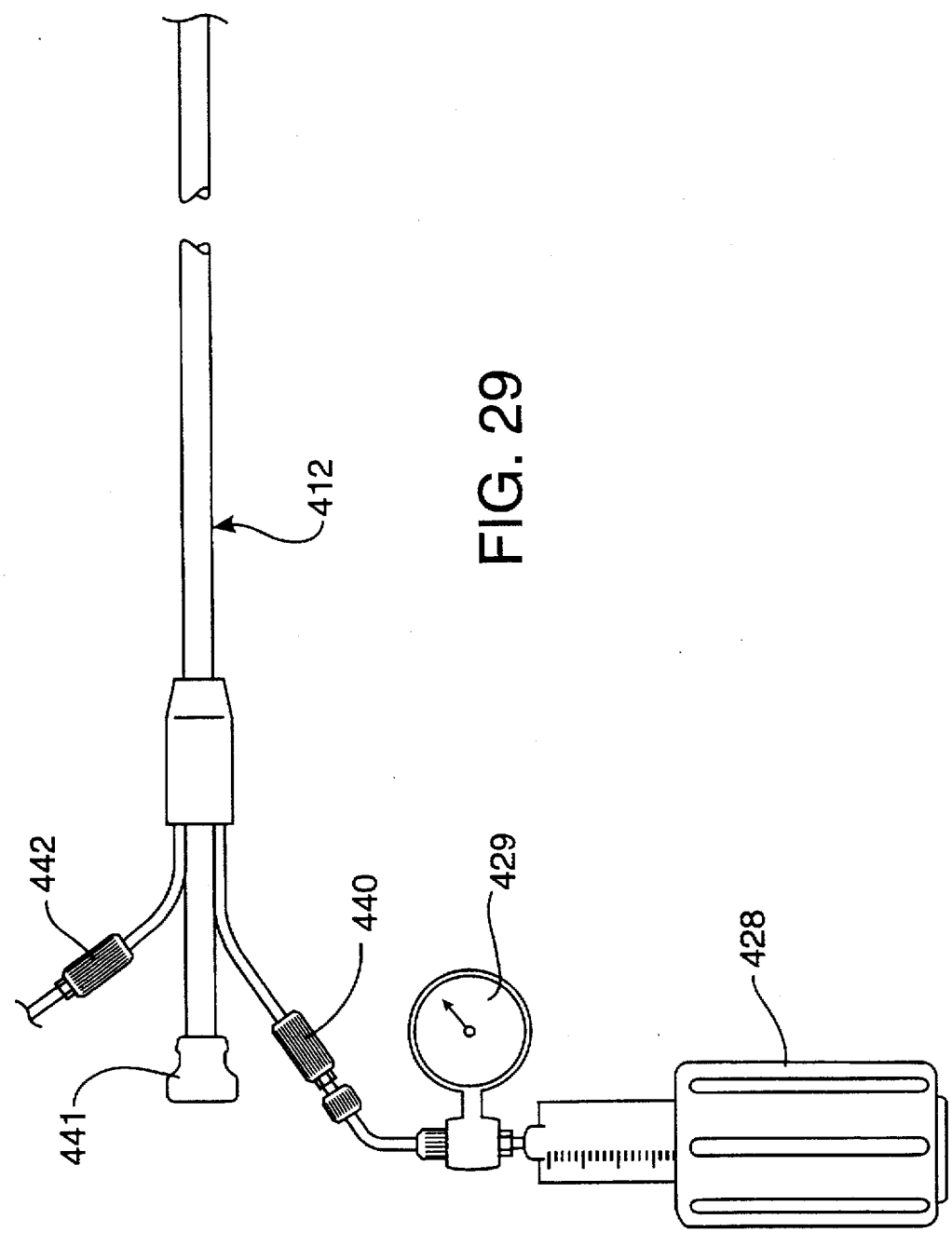
FIG. 29 is a side elevational view of the control end of the aortic catheter according to the present invention.

The catheter 412 is positioned in the manner described above with its free end located in the ascending aorta 423. The catheter 412 is so positioned by insertion preferably through the femoral artery 424 and via the descending aorta 425 as is seen in FIG. 28.

If desired a fluoroscopic dye may be introduced into the aortic root 426 through the catheter 412 for accurate positioning of the tip of the catheter 412 relative to the aortic root 426 and the coronary ostia.

The catheter 412 carries at its free end a balloon 427. The balloon 427 is arranged to be inflated with saline from an inflation control device 428 of known type through a lumen in the catheter 412. The device 428 is fitted with a pressure gauge 429 to allow the operator to control the inflation of the balloon 427. The pressure of the fully inflated balloon 427 should be of the order of 350 mmHg so as to be sufficient to effectively occlude the aorta and to prevent the balloon moving while not being so great as to cause damage to the aortic wall. The balloon 427 should have a maximum diameter sufficient to occlude the aorta and for this purpose the maximum diameter should be about 35 mm. The balloon 427 should have a length of about 40 mm so as not to be so long as to occlude or impede blood flow to the coronary arteries or to the brachiocephalic, subclavian or carotid arteries. If necessary in any given patient the required length and diameter of the balloon may be determined by angiographic, X-ray examination or echocardiography and an appropriately sized catheter selected on that basis.

The balloon 427 is preferably connected to the lumen 432 through which it is inflated at the end of the balloon 427 distal to the tip of the catheter 412 through orifice 431 (see FIG. 30). This allows the tip of the catheter to contain fewer lumina than the remainder of the catheter. Accommodation of the deflated balloon around the tip of the catheter is thus possible without adding to the diameter of the tip as compared with the rest of the catheter 412.

The catheter 412 includes a plurality of lumina (see FIGS. 31 and 32). In addition to the balloon inflation lumen 432 there is at least a single venting/cardioplegia lumen 433 of circular cross-section. There may be a separate and extra circular lumen 434 for instrumentation. If two lumens are present the venting/cardioplegia lumen may be circular or crescent shaped in cross-section (FIG. 31a, 31b). The diameter of the various lumina should be as small as practicable commensurate with the intended use. In addition, there may be a continuous lumen 435 through which arterial blood is returned from the by-pass. This may flow out of the catheter 412 through an orifice in the region of the external iliac artery. In alternative embodiments of the invention such as shown in FIGS. 28 and 33b the arterial return lumen 435 may comprise its own catheter 439 of known type introduced into the other femoral artery or some other suitable artery.

In use the catheter 412 is introduced percutaneously by puncture or cutdown as has been described and once blood flow through the by-pass is established (including systemic cooling) flows are reduced and the balloon 425 is inflated. Flows are then returned to the operating levels and a suitable cardioplegic agent is introduced into the aortic root. Once the full volume of cardioplegic agent has been given and cardiac arrest achieved, the lumen is then used to vent the heart. Venting of the left ventricle may be effected by providing an extended cannula 438 projecting from lumen 433 into the left ventricle (see FIG. 27) or by simply applying negative pressure to the venting lumen 433 of the aortic catheter. The heart may then be operated on or examined by insertion of instrumentation 437 such as a cardioscope or a laser into the heart through the lumen 434 or through atrial trocars. Alternatively, with the heart on by-pass as described above the heart can be approached by an open method by an incision other than median sternotomy.

With cardiopulmonary bypass established, cardiac function arrested, and the right lung collapsed, the patient is prepared for surgical intervention within the heart H. A preferred technique of mitral valve replacement will be described in detail here. Referring again to FIG. 2, a surgical cutting instrument such as angled scissors 110, as well as a grasping instrument such as grasping forceps 112, are introduced through access cannula 22 or through trocar sleeves 24A, 24B. Angled scissors 110 and forceps 112 are used to form an opening in the pericardium, providing access to the right side of the left atrium.

Angled scissors 110 are illustrated more clearly in FIGS. 12A–12D. Angled scissors 110 include a shaft 114 having a distal end 116, a proximal end 118, and an actuator 120 attached to proximal end 118. Shaft 114 of angled scissors 110 has a length selected to allow intervention within left atrium LA of heart H, and is usually at least about 15 cm in length and preferably 20 cm to 35 cm in length. Actuator 120 includes a movable arm 122 pivotally coupled to a stationary arm 124. A linkage 126 connects movable arm 122 to a push rod 128 extending slidably through shaft 110. By pivoting movable arm 122 toward shaft 114, push rod 128 is translated distally. A stationary blade 130 is mounted to distal end 116 of shaft 114, and a movable blade 132 is pivotally mounted to stationary blade 130. Push rod 128 is linked to movable blade 132 such that distal movement of push rod 128 pivots movable blade 132 toward stationary blade 130. Blades 130, 132 may be mounted at various angles relative to shaft 114, as illustrated in FIGS. 12B–12D. A flush port (not shown) may also be provided in shaft 114 for delivering a flushing solution such as saline to distal end 116 to remove fluid and/or debris from blades 130, 132 or from the surgical site.

In addition to angled scissors 110, a retractable knife 134, illustrated in FIG. 13, may be used for various cutting purposes. Retractable knife 134 comprises a shaft 136 having a distal end 138 and a proximal end 140. A handle 142 is attached to proximal end 140, to which an actuator 144 is slidably mounted. A push rod (not shown) is coupled to actuator 144 and extends slidably through shaft 136. A knife blade 146 is slidably mounted at distal end 138 of shaft 136 and is linked to the push rod, such that sliding actuator 144 proximally retracts knife blade 146 within a sheath 148 mounted to distal end 138. Alternatively, knife blade 146 may be fixed to shaft 136, and sheath 148 slidably mounted to shaft 136 and linked to the push rod, such that sheath 148 may be retracted and extended over knife blade 146 by sliding actuator 144.

Grasping forceps 112 are illustrated in FIGS. 14A–14B. Grasping forceps 112 have a construction much the same as that of angled scissors 110, with an actuator 150 translating a push rod 152 slidably disposed in a shaft 154. A stationary jaw 158 is fixed to a distal end 156 of shaft 154, and a movable jaw 160 is slidably mounted to shaft 154. Push rod 152 is linked to movable jaw 160, such that translation of push rod 152 by actuator 150 closes movable jaw 160 against stationary jaw 158. Grooves or other textural features may be provided on the inner surfaces of jaw 158 and/or jaw 160 to improve grip upon tissue.

Figure 4:
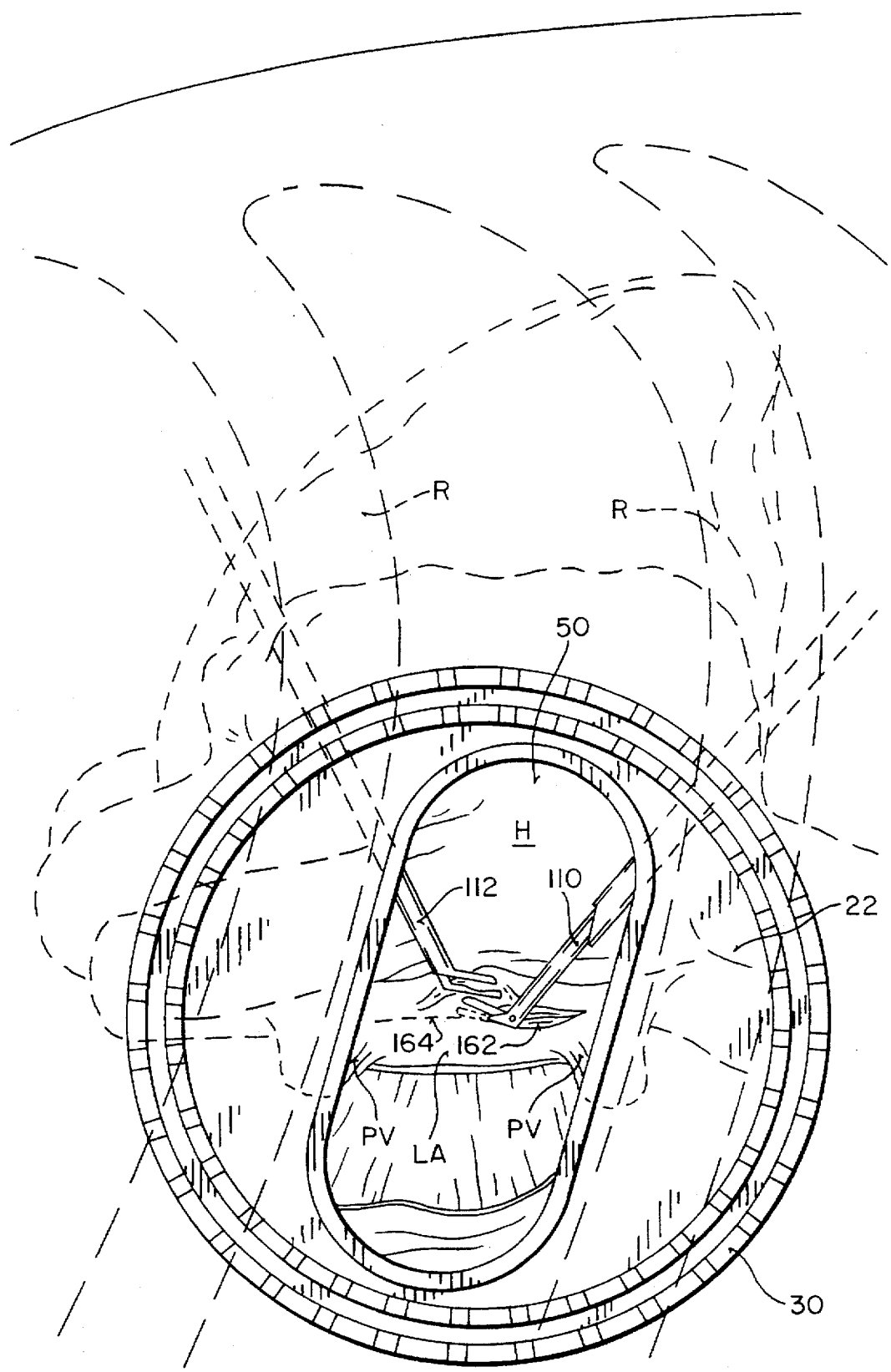
FIG. 4 is a top view looking into the patient's thoracic cavity through a passage of an access cannula in the system of FIG. 1, showing the creation of an atriotomy in the patient's left atrium.

FIG. 4 illustrates the view into the thoracic cavity through passage 50 of access cannula 22. Angled scissors 110 aided by grasping forceps 112 are shown cutting through the right side of left atrium LA to form an atriotomy 162. Atriotomy 162 is formed along dotted line 164 anterior to right pulmonary veins PV. A completed description of techniques for forming such an atriotomy is found in Kirklin and Barratt-Boyes, *Cardiac Surgery*, pp. 329–340, the disclosure of which has been incorporated herein by reference. Usually, atriotomy 162 will be formed under visualization by means of endoscope 25 (FIGS. 1 and 2), although direct viewing is possible through passage 50 of access cannula 22, or through a trocar sleeve 24.

Figure 5:
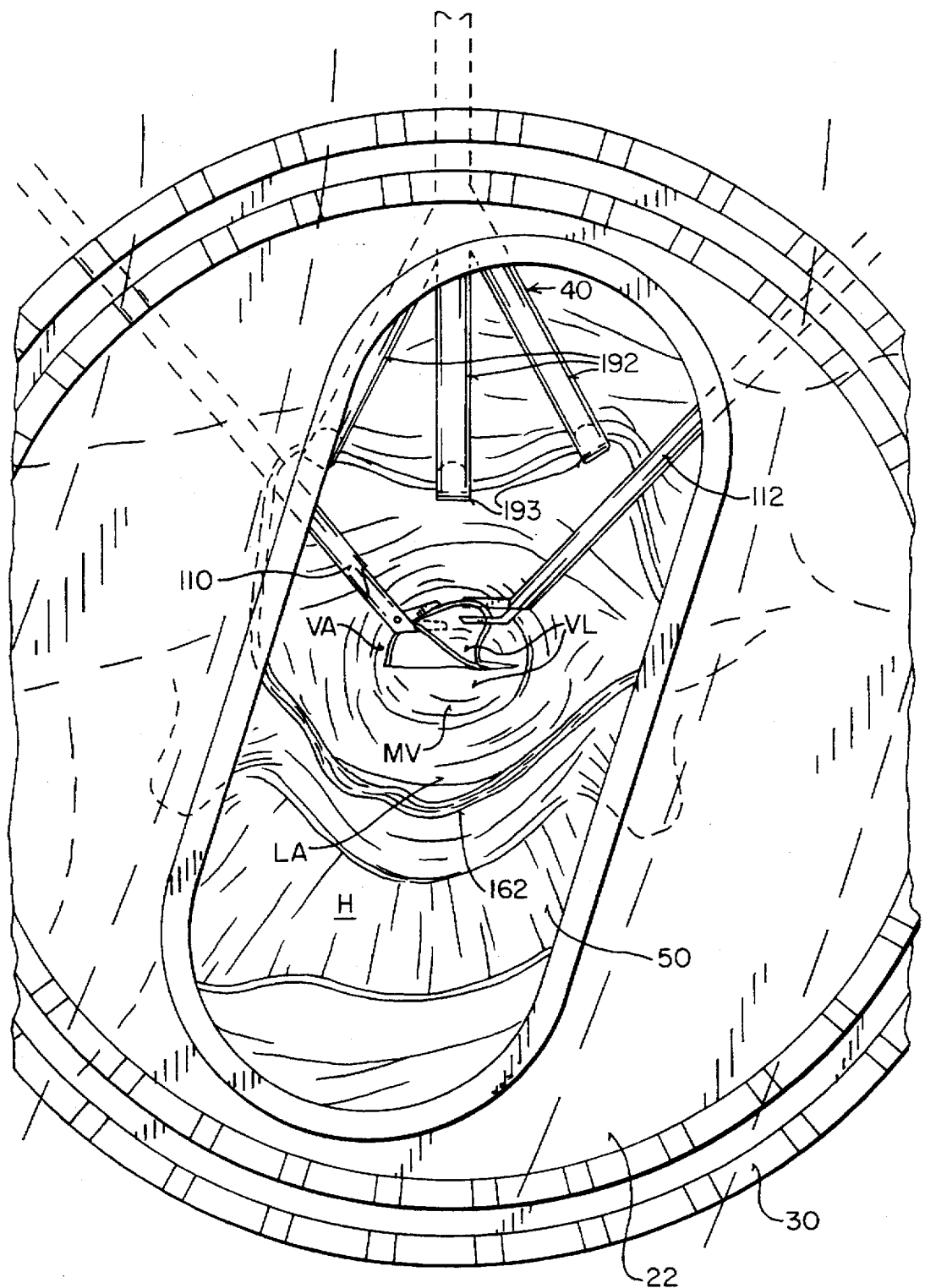
FIG. 5 is a top view looking into the patient's thoracic cavity through a passage of an access cannula in the system of FIG. 1, showing the removal of the mitral valve leaflets.

Upon completion of atriotomy 162, the wall of left atrium LA on the anterior side of atriotomy 162 is retracted anteriorly by means of thoracoscopic retractor 40, as illustrated FIGS. 1 and 5. Thoracoscopic retractor 40, illustrated more clearly in FIG. 15, includes a shaft 166 having a distal end 168, a proximal end 170, and an inner lumen 172 therebetween. A pair of finger rings 174 is mounted to proximal end 170 of shaft 166. A guide 175 is also mounted to proximal end 170 having a channel 176 extending therethrough. A sliding rod 178 extends through channel 176 and has a plurality of teeth 180 on a lateral surface thereof which are engaged by a pawl 182 pivotally mounted to guide 175 and biased by a spring (not shown) against teeth 180. Sliding rod 178 has a proximal end 184 to which a thumb ring 186 is attached, allowing thumb ring 186 to be drawn toward finger rings 174. A push rod 188 is slidably disposed in lumen 172 of shaft 166 and is attached at its proximal end 190 to sliding rod 178. Three rake arms 192 are pivotally coupled to shaft 166 within a transverse slot 194 at distal end 168. Rake arms 192 each have a hooked distal end 193 for engaging and retracting tissue. The distal end of push rod 188 slidably engages rake arms 192 within a slot 196 in each rake arm. In this way, by sliding push rod 188 distally, rake arms 192 collapse in an overlapping configuration suitable for introduction through one of trocar sleeves 24. Once rake arms 192 are introduced into the thoracic cavity, they may be expanded by pulling thumb ring 186 relative to finger rings 174.

Referring again to FIG. 5, retractor 40 is introduced into the thoracic cavity through trocar sleeve 24 and rake arms 192 are deployed into their expanded configuration. Retractor 40 is manipulated so that hooked ends 193 of rake arms 192 engage the wall of left atrium LA on the anterior side of atriotomy 162. Retractor 40 is then pulled in the anterior direction to retract the wall of left atrium LA, opening atriotomy 162 and exposing the patient's mitral valve MV within the left atrium LA. A conventional stopcock, cam lock, or other clamping device (not shown) may be provided on trocar sleeve 24 to lock retractor 40 in position, or shaft 166 may be provided with an adjustable collar (not shown) for engaging trocar sleeve 24 to maintain retractor 40 in position.

Figure 15:
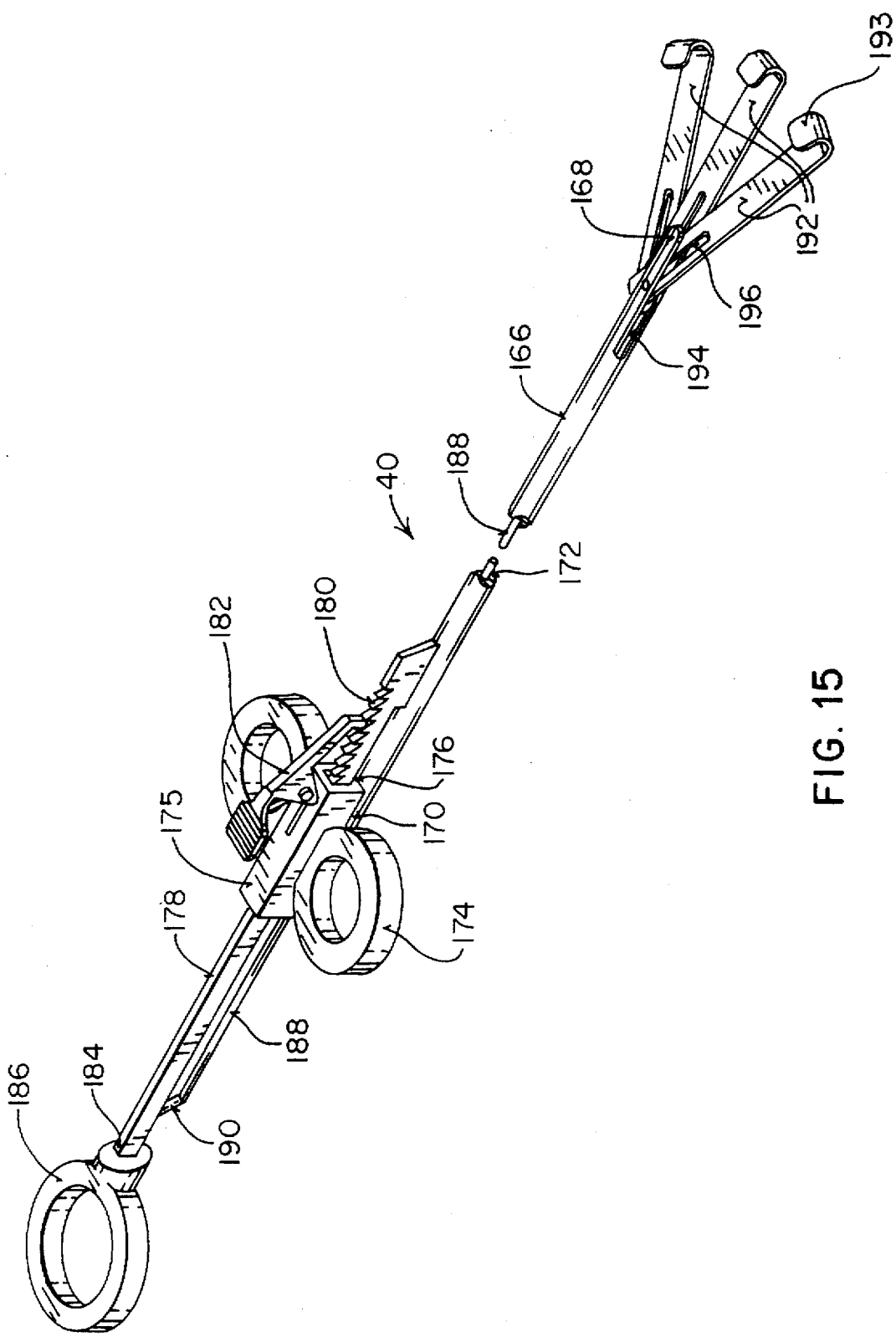
FIG. 15 is a perspective view of a left atrial retractor in the system of FIG. 1.

It will be understood that retractor 40 illustrated in FIGS. 1, 5 and 15 is merely exemplary of the various means that may be used for retraction of left atrium LA. Another suitable means of retraction is described in published European patent application number PCT/US92/06186, the complete disclosure of which is incorporated herein by reference. That application describes a clip which may be applied to tissue by means of an introducer, and a flexible cable assembly attached to the clip which may be used to apply traction to the clip from outside of the patient's body. The clip may be applied to the wall of the left atrium LA on the anterior side of atriotomy 162 with the cable extending through a trocar sleeve 24, whereby atriotomy 162 is retracted open by applying traction to the cable. The cable may be attached to the patient's body, to the surgical drapes, or to another support structure outside of the body to maintain the atriotomy open during the procedure. Alternatively, one or more sutures (not shown) may be applied to the wall of left atrium LA anterior to atriotomy 162. The free ends of the sutures may be applied to an internal structure in the thoracic cavity, or withdrawn from the thoracic cavity through a puncture or a trocar sleeve 24 and attached to the patient's body or to the surgical drapes, thereby opening atriotomy 162. Other suitable means of retraction include devices having a collapsible and expandable frame (not pictured) which is insertable within atriotomy 162. When deployed, the frame urges the opposing sides of atriotomy 162 away from each other, and maintains the atriotomy open throughout the procedure until the device is removed.

With atriotomy 162 retracted open, the interior of heart H is accessible for the performance of an interventional procedure therein. Instruments may be introduced through access cannula 22 or trocar sleeves 24 and through atriotomy 162 to perform a procedure within left atrium LA. Additionally, such instruments may be extended through mitral valve MV into the left ventricle, or from the left ventricle through the aortic valve into the ascending aorta for inspection or intervention therein. In this way, the aortic valve may be repaired or replaced using techniques much like the mitral valve repair and replacement techniques described below.

When replacing mitral valve MV, it is often desirable to cut or remove all or a portion of the mitral valve leaflets VL. For this purpose, grasping forceps 112 may be used to grasp valve leaflet VL while angled scissors 110 and/or knife 134 are used to excise valve leaflet VL from the valve annulus VA. All or part of one or both valve leaflets VL may be cut or removed in this way. When removing valve leaflets VL, however, it is generally desirable to avoid permanently cutting or removing the chordae tendonae and papillary muscles (not shown) attached to the left ventricle. It has been found that a patient's chordae tendonae and papillary muscles may contribute to proper cardiac function even when a patient's natural valve has been replaced with a replacement valve.

At this point, it is usually necessary to size valve annulus VA so as to select a replacement valve 36 of the proper size for patient P. Various means may be used for sizing, but in one embodiment a sizing disk is introduced through access cannula 22, and the diameter of the sizing disk is compared to that of valve annulus VA. Preferred devices and methods for sizing valve annulus VA are described more fully below.

Figure 6:
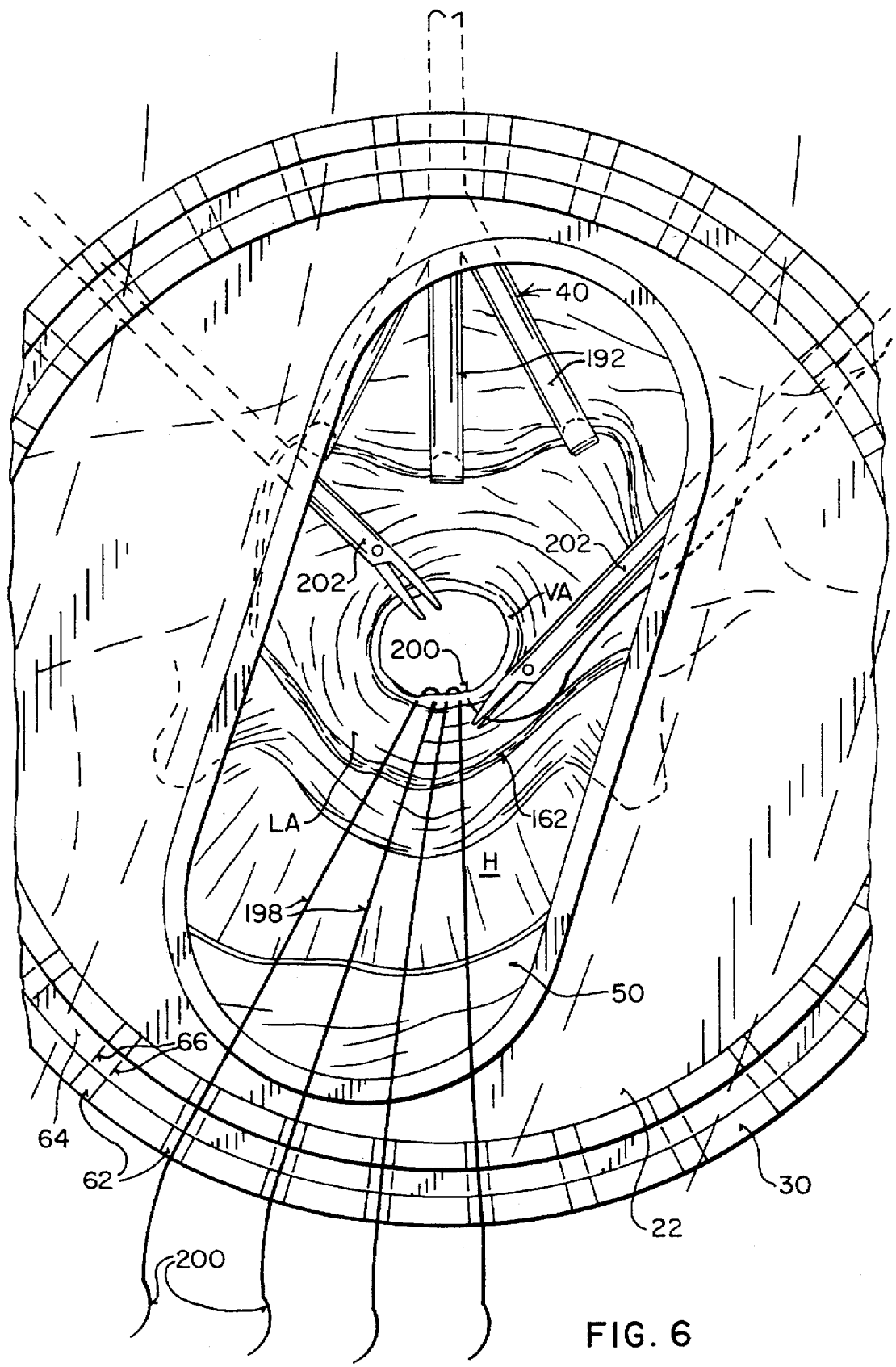
FIG. 6 is a top view looking into the patient's thoracic cavity through a passage of an access cannula in the system of FIG. 1, showing the application of sutures to the mitral valve annulus.

Various types of replacement valves are available for replacement of the mitral valve, and there are various ways of securing these replacement valves within the patient's heart. One common means of replacement valve attachment is suturing the prosthesis to the patient's natural valve annulus. Referring to FIG. 6, after valve leaflets VL have been removed, a plurality of sutures 198 are applied to valve annulus VA, under visualization by means of endoscope 25 (FIGS. 1–2) and/or by direct vision through passage 50 of access cannula 22. Each end of each suture 198 is attached to a curved needle 200. At least one and usually two needle drivers 202 are introduced into the thoracic cavity through trocar sleeves 24 and/or access cannula 22. A first of needle drivers 202 is used to drive a tip of needle 200 through valve annulus VA, while a second of needle drivers 202 is used to grasp the tip of needle 200 and pull it completely through valve annulus VA. After being applied to valve annulus VA, each suture 198 is withdrawn from the thoracic cavity through passage 50 of access cannula 22, and placed in one of slots 62 in organizing ring 30. Because a needle 200 is attached to both ends of each suture 198, each needle 200 may be driven through valve annulus VA in a single direction, then withdrawn from the thoracic cavity through passage 50 of access cannula 22. Preferably, each suture 198 is positioned within a slit 66 in retaining ring 64 (FIGS. 11A–11D) to frictionally engage the suture and keep it within slot 62.

Various types of stitches may be used in applying sutures 198 to valve annulus VA. In an exemplary embodiment, a "mattress" suture technique is used, wherein each needle 200 is driven through valve annulus VA from the ventricular side toward the atrial side of valve annulus VA. Alternatively, an "everting mattress" suture technique is used, wherein each needle 200 is driven through valve annulus VA from the atrial side toward the ventricular side of valve annulus VA. Various other types of stitches may also be used, depending upon the type of replacement valve to be utilized and the position in which it is to be mounted to valve annulus VA.

FIGS. 16A–16B illustrate the construction of needle drivers 202 in greater detail. Needle drivers 202 include a shaft 204 having a distal end 206 and a proximal end 208. An actuator 210 is attached to proximal end 208, and is constructed as described above in connection with FIG. 12A. Actuator 210 translates a push rod 212 extending through shaft 204. A stationary jaw 214 is fixed to distal end 206 of shaft 204, and a movable jaw 216 is pivotally mounted to stationary jaw 214. Movable jaw 216 is linked to push rod 212, whereby distal movement of push rod 212 closes movable jaw 216 against stationary jaw 214. Carbide surfaces as well as grooves or other textural features may be provided on the inner surfaces of jaws 214, 216 to enhance gripping of needles 200. Further, a locking mechanism (not shown) may be included on actuator 210 to lock jaws 214, 216 in the closed position.

Figure 7:
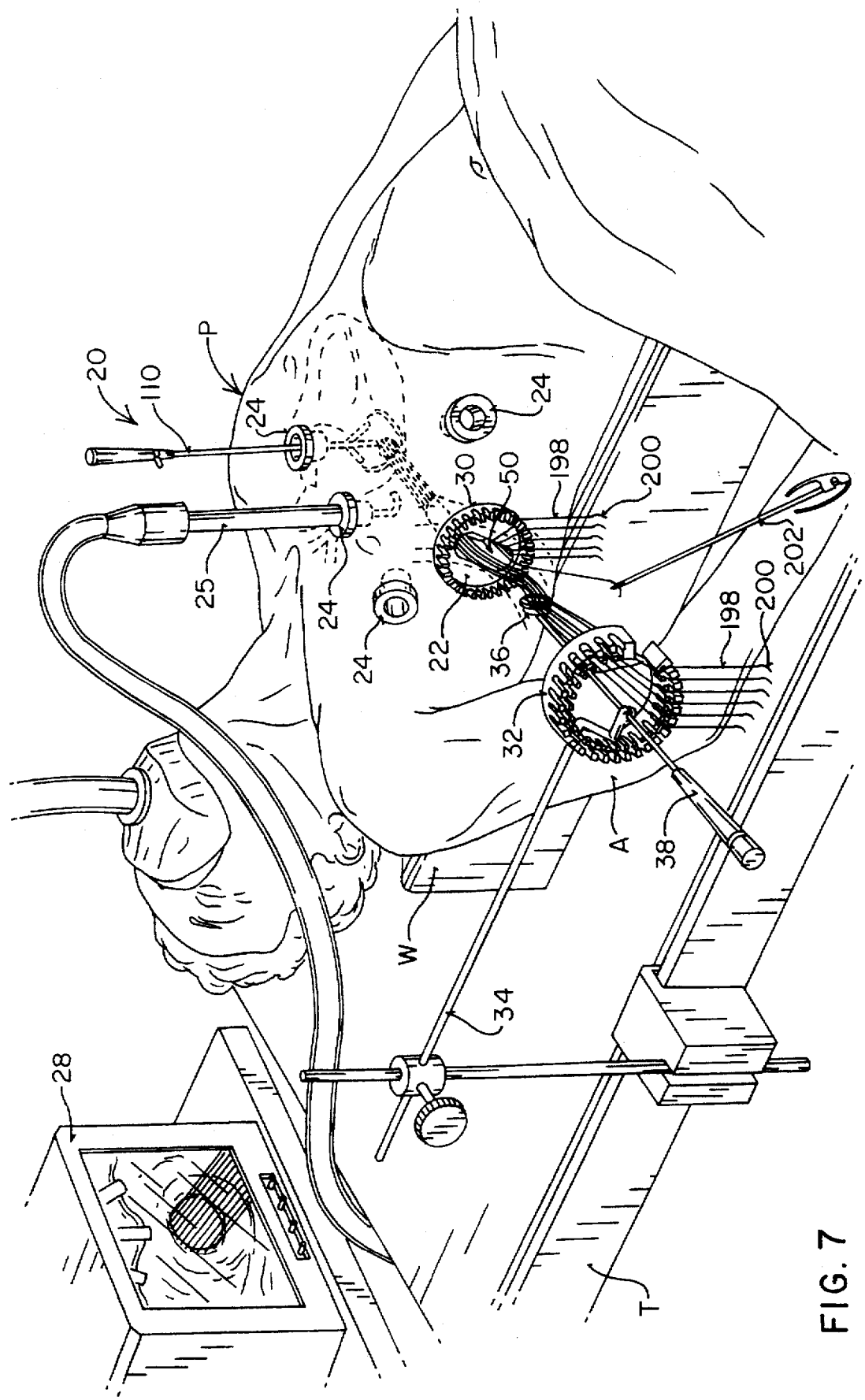
FIG. 7 is a perspective view of the system of FIG. 1 positioned in the patient, showing the application of sutures to a replacement valve.

Referring to FIG. 7, once all of sutures 198 have been withdrawn from the thoracic cavity and placed in slots 62 of organizing ring 30, the sutures are applied to replacement valve 36, held in position by introducer 38. Replacement valve 36 may be any of a variety of commercially available prostheses, including mechanical and bioprosthetic, stented and unstented, as described in Bodnar and Frater, *Replacement Cardiac Valves*, pp. 4–7, which has been incorporated herein by reference, and in Jamieson, "Modern Cardiac Valve Devices—Bioprostheses and Mechanical Prostheses: State of the Art," *J. Card. Surg.* 8:89–98 (1993). Mechanical valves may be of the caged ball type such as the Starr-Edwards valve (Baxter Healthcare Corp., Edwards CVS Div., Irvine, Calif.), the tilting disk type such as the Medtronic Hall valve (Medtronic, Inc., Minneapolis, Minn.), the Bjork-Shiley Monostrut valve (Shiley, Inc., Irvine, Calif.), the Omniscience® valve (Omniscience Medical Inc., Grove Heights, Minn.), as well as the bileaflet type such as the St. Jude Medical valve (St. Jude Medical, Inc., St. Paul, Minn.), the Baxter Duromedics valve (Baxter Healthcare Corp., Edwards CVS Div., Irvine, Calif.), the Carbomedics valve (Carbomedics, Inc., Austin, Tex.), or the Sorin valve (Sorin Biomedica, Saluggia, Italy). Bioprosthetic valves may be porcine aortic valves such as the Hancock II bioprosthesis (Medtronic, Inc., Minneapolis, Minn.), the Carpentier-Edwards supraannular bioprosthesis (Baxter Healthcare Corp., Edwards CVS Div., Irvine, Calif.), the Carpentier-Edwards stentless bioprosthesis (Baxter Healthcare Corp., Edwards CVS Div., Irvine, Calif.), the St. Jude-Bioimplant bioprosthesis (St. Jude Medical, Inc., St. Paul, Minn.), or the Medtronic Intact® bioprosthesis (Medtronic, Inc., Minneapolis, Minn.), as well as pericardial valves such as the Mitroflow bioprosthesis (Mitroflow International, Inc., Richmond, British Columbia, Canada), or the Carpentier-Edwards pericardial bioprostheses (Baxter Healthcare Corp., Edwards CVS Div., Irvine, Calif.). The invention also facilitates valve replacement with homografts and allografts, as well as with a variety of replacement valves not specifically listed here.

In an exemplary embodiment, the invention facilitates replacement of a patient's mitral valve with a mechanical bileaflet replacement valve such as the St. Jude Medical valve, illustrated in FIGS. 17A–17C. In this embodiment, replacement valve 36 comprises a ring-shaped frame 218 and a pair of leaflets 220 pivotally mounted to frame 218. In the open configuration illustrated in FIGS. 17A–17B, leaflets 220 are nearly parallel to each other, providing a flow passage 222 through which blood may flow in the direction of arrows 224. In the event of fluid pressure against the inner faces 226 of leaflets 220, leaflets 220 pivot into a closed configuration, blocking flow passage 222. A sewing ring 228 is attached to frame 218 to which sutures 198 may be applied for securing replacement valve 36 in the heart.

Figure 17A:
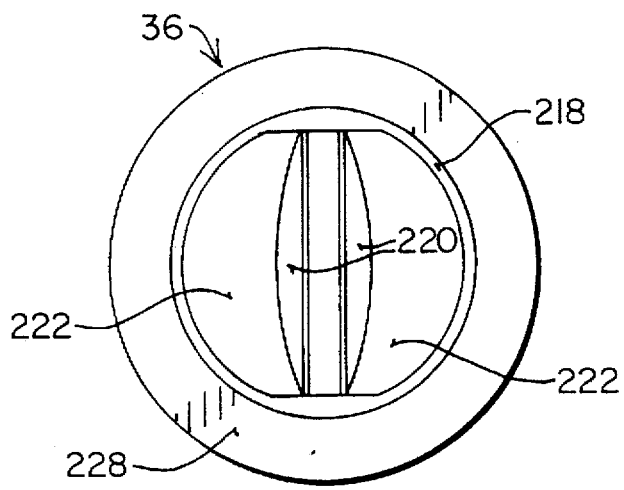
FIGS. 17A–17B are top and side views, respectively, of a replacement valve in the system of FIG. 1.
Figure 17C:
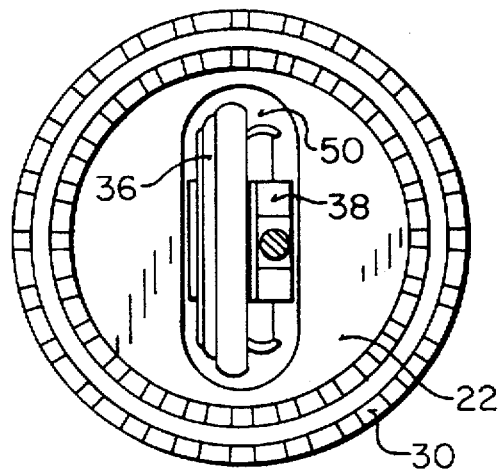
FIG. 17C is an end view of the replacement valve of FIGS. 17A–17B positioned in a passage of an access cannula in the system of FIG. 1.
Figure 17B:
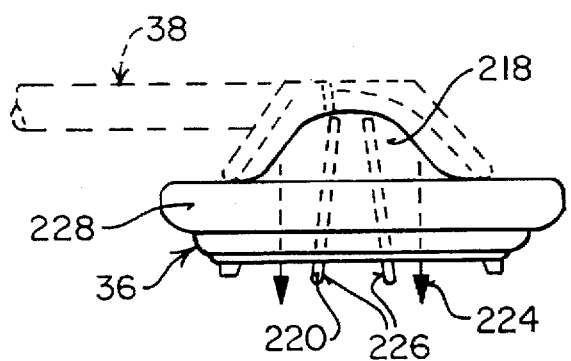

As illustrated in FIGS. 17B–17C, replacement valve 36 may be mounted to introducer 38 for introduction into the heart through passage 50 of access cannula 22. Replacement valve 36 may have various sizes according to the size of the mitral valve being replaced. However, the outer diameter of sewing ring 228 is usually about 19 mm to 35 mm, which, for most adult patients, is larger than the width of the third, fourth, fifth or sixth intercostal spaces, which range from 15 mm to 20 mm in width. The height of replacement valve 36, on the other hand, is smaller than the width of these intercostal spaces, usually being about 8 mm to 15 mm. Therefore, passage 50 is configured to allow replacement valve 36 to pass through it in an edge-first orientation, as illustrated in FIG. 17C.

Figures 18, 21:
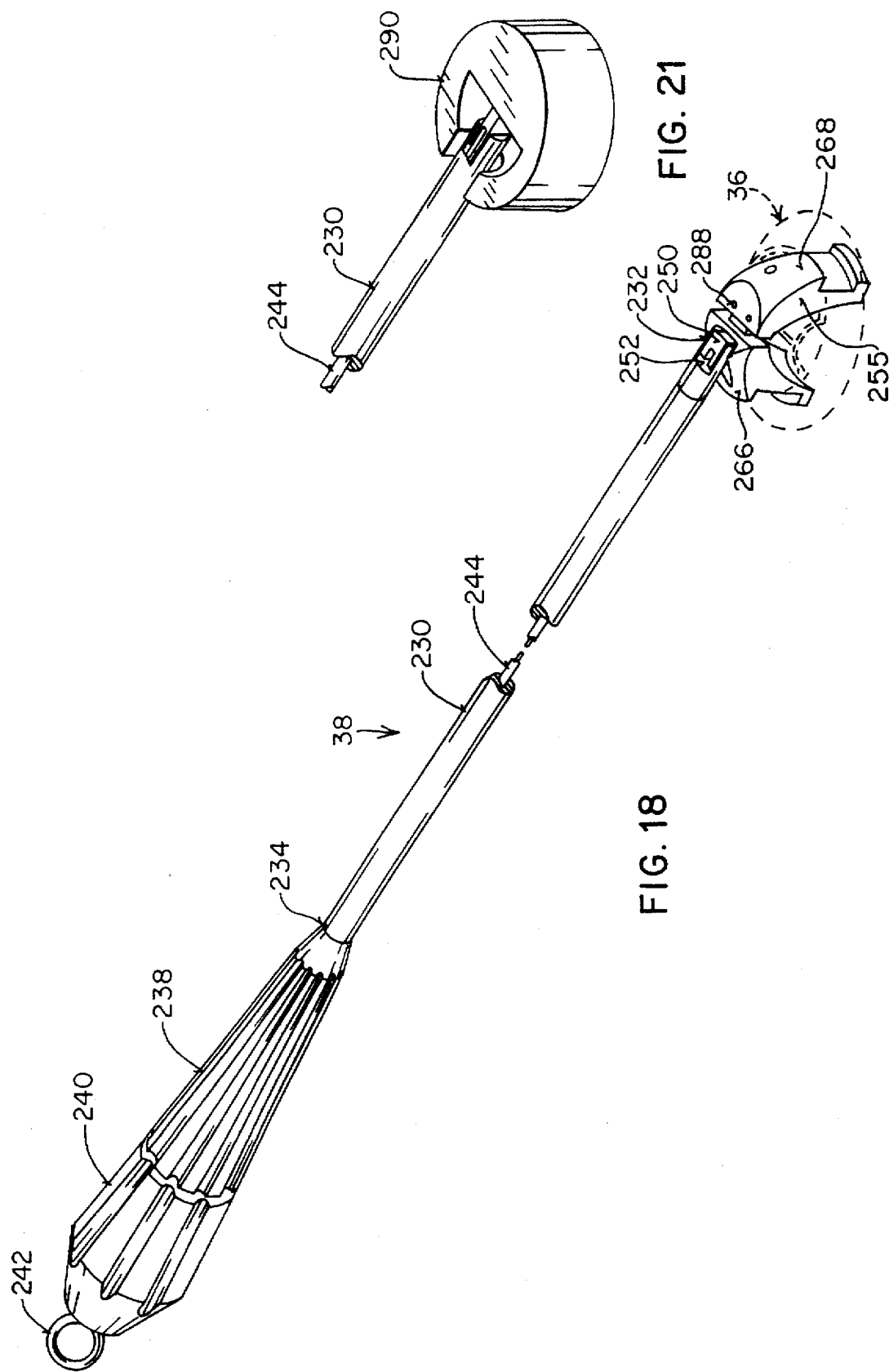
FIG. 18 is a perspective view of a prosthesis introducer in the system of FIG. 1.
FIG. 21 is a perspective view of a sizing disk in the system of FIG. 1, positioned on the introducer of FIG. 18.

Introducer 38 will now be described with reference to FIGS. 18–20. Introducer 38 includes a shaft 230 having a distal end 232, a proximal end 234, and an inner lumen 236 therebetween. Shaft 230 has a length selected to allow placement of replacement valve 36 in the mitral valve position within the patient's heart from outside of the patient's thoracic cavity, and is usually at least about 20 cm in length, and preferably about 25 cm to 35 cm in length. A handle 238 is attached to proximal end 234, and a rotatable knob 240 is mounted to handle 238 for pivoting the replacement valve 36 relative to shaft 230. A pull ring 242 extends proximally from pivot knob 240 for releasing replacement valve 36 from introducer 38. As best seen in FIGS. 20A–20B, push rod 244 extends through inner lumen 236, and is coupled at its distal end 248 to a pivot 250 which is pivotally mounted within a slot 252 at distal end 232 of shaft 230. A shank 254 extends distally from pivot 250 and has threads or other means for attachment to a valve holder 255 for replacement valve 36. Knob 240 is fixed to a threaded shaft 256 received within a threaded bore 258 in handle 238, whereby rotation of knob 240 translates threaded shaft 256 distally or proximally, depending upon the direction of rotation. Push rod 244 has a proximal end 260 which engages a distal end 262 of threaded shaft 256. A spring 264 biases push rod 244 in a proximal direction against distal end 262. In this way, rotation of knob 240 pulls or pushes push rod 244, thereby pivoting pivot 250 such that shank 254 extends either distally or laterally.

Referring to FIGS. 19A–19G, valve holder 255 includes a stationary arm 266 attached to shank 254, and a movable arm 268 pivotally mounted to stationary arm 266. Each of arms 266, 268 has an annular channel 270 configured to engage frame 218 of replacement valve 36 within flow channel 222 (FIG. 17A). Arms 266, 268 are further dimensioned and configured for introduction through passage 50 of access cannula 22 when replacement valve 36 is held in channels 270. As illustrated in FIG. 19A, when attached to shank 254 on introducer 38, valve holder 255 may be pivoted in the direction of arrow 272 by rotation of knob 240. In this way, the replacement valve 36 held by holder 255 may be introduced edge-first through passage 50 in access cannula 22, then pivoted approximately 90° to an orientation suitable for attachment in the mitral valve position within heart H.

To facilitate releasing replacement valve 36 from holder 55 from a location outside of the patient's body, a pull wire 274 is coupled to movable arm 268 by, for example, an anchor ball 276 disposed within an aperture 278 (see FIG. 20A). Pull wire 274 extends through an inner lumen (not shown) in push rod 244, and is attached at its proximal end 280 to pull ring 242. A spring 282 within an aperture 284 in knob 240 biases pull ring 242 in a distal direction. In this way, pulling on pull ring 242 pivots movable arm 268 as shown in FIG. 19C, allowing replacement valve 36 to be removed from channels 270. Anchor ball 276 and/or pull ring 242 may be configured so as to be removable from pull wire 244, allowing valve holder 255 to be removed from introducer 38 by decoupling arm 266 from shank 254.

In order 16 keep replacement valve 36 on holder 255 when holder 255 is not attached to introducer 38, a pair of holes 286 are provided in arm 266 in alignment with a corresponding pair of holes 288 in arm 268. When replacement valve 36 has been placed on holder 255, a suture (not shown) may be tied through holes 286, 288 to prevent pivoting of arm 268, thereby retaining replacement valve 36 on holder 255. Once holder 255 has been attached to introducer 38, the suture may be removed, allowing arm 268 to pivot in response to rotation of knob 240.

It will frequently be desirable for valve holder 255 and replacement valve 36 to be pre-assembled, sterilized, and packaged together in a single sterile pack. In this way, upon opening the sterile pack in the operating room, the replacement valve 36 and holder 255 are ready for immediate surgical use. Further, it may be desirable for introducer 38 to be sterilized with replacement valve 36 and included in the same sterile pack. In such cases, holder 255 may be integrated with and non-removable from introducer 38, with replacement valve 36 being mounted to arms 266, 268 at the distal end of introducer 38 within the sterile pack. Alternatively, introducer 38 may be a reusable device which is attached to holder 255 and replacement valve 36 in the operating room at the time of the procedure.

As mentioned above, in order to select a replacement valve 36 which is of the appropriate size for patient P, valve annulus VA is usually sized prior to applying sutures 198 to valve annulus VA. Sizing may be accomplished in various ways, but in an exemplary embodiment, is performed by means of a sizing disk 290, illustrated in FIGS. 21–23, pivotally attached to introducer 38. Sizing disk 290 may be pivoted approximately 90° relative to shaft 230 of introducer 38, from an edge-first orientation suitable for introduction through access cannula 22, to a face-first orientation suitable for sizing valve annulus VA. As shown in FIGS. 22 and 23, sizing disk 290 is configured for attachment to shank 254 of introducer 38, preferably by means of a threaded hole 292. A notch 294 is provided in a proximal portion of disk 290 through which distal end 232 of shaft 230 may extend when disk 290 is in the edge-first orientation. An aperture 296 is disposed in the middle of disk 290 through which distal end 232 of shaft 230 may extend when disk 290 is in the face-first orientation. Preferably, a plurality of interchangeable sizing disks 290 of various diameters are provided for the procedure, allowing various sizing disks 290 to be introduced into heart H and compared with valve annulus VA until the diameter of the sizing disk corresponds to that of valve annulus VA.

In place of sizing disk 290, an expandable balloon or basket may be used for sizing valve annulus VA. Fluoroscopy, transesophageal echocardiography (TEE), epicardial or trans-thoracic ultra-sonography, or angiography may also be used to facilitate sizing valve annulus VA.

When the size of valve annulus VA has been identified, sizing disk 290 may be removed from introducer 38 and replaced by a replacement valve 36 of the appropriate size, mounted on holder 255. Introducer 38 may then be clamped to support stand 34 with replacement valve 36 positioned between first organizing ring 30 and second organizing ring 32, as illustrated in FIG. 7.

Sutures 198 are applied to replacement valve 36 by passing needles 200 through sewing ring 228 using needle drivers 202. Sutures 198 are then positioned in circumferentially spaced positions on second organizing ring 32. Second organizing ring 32 comprises, as illustrated in FIGS. 24A–24C, an inner ring 298 fixed to support stand 34, and an outer ring 300 rotatably mounted to inner ring 298. An elastomeric retaining ring 302 is disposed in an annular channel 304 in inner ring 298. Radial pins 303 are fixed to inner ring 298 and extend through slots 305 in outer ring 300, thereby limiting the rotation of outer ring 300 relative to inner ring 298. A plurality of slots 306 are disposed in circumferentially spaced positions about inner ring 298, and a corresponding number of slots 308 alignable with slots 306 are disposed in outer ring 300. Retaining ring 302 has a plurality of slits 310 which are aligned with slots 306 in inner ring 298. A clamp 312 for clamping shaft 230 of introducer 38 is disposed on an extension 314 fixed to support stand 34.

After being applied to replacement valve 36, sutures 198 may be positioned within inner slots 306, slits 310, and outer slots 308. Once all of sutures 298 have been applied to replacement valve 36 and positioned in organizing ring 32, outer ring 300 may be rotated relative to inner ring 298, thereby locking sutures 298 in position.

Figure 8A:
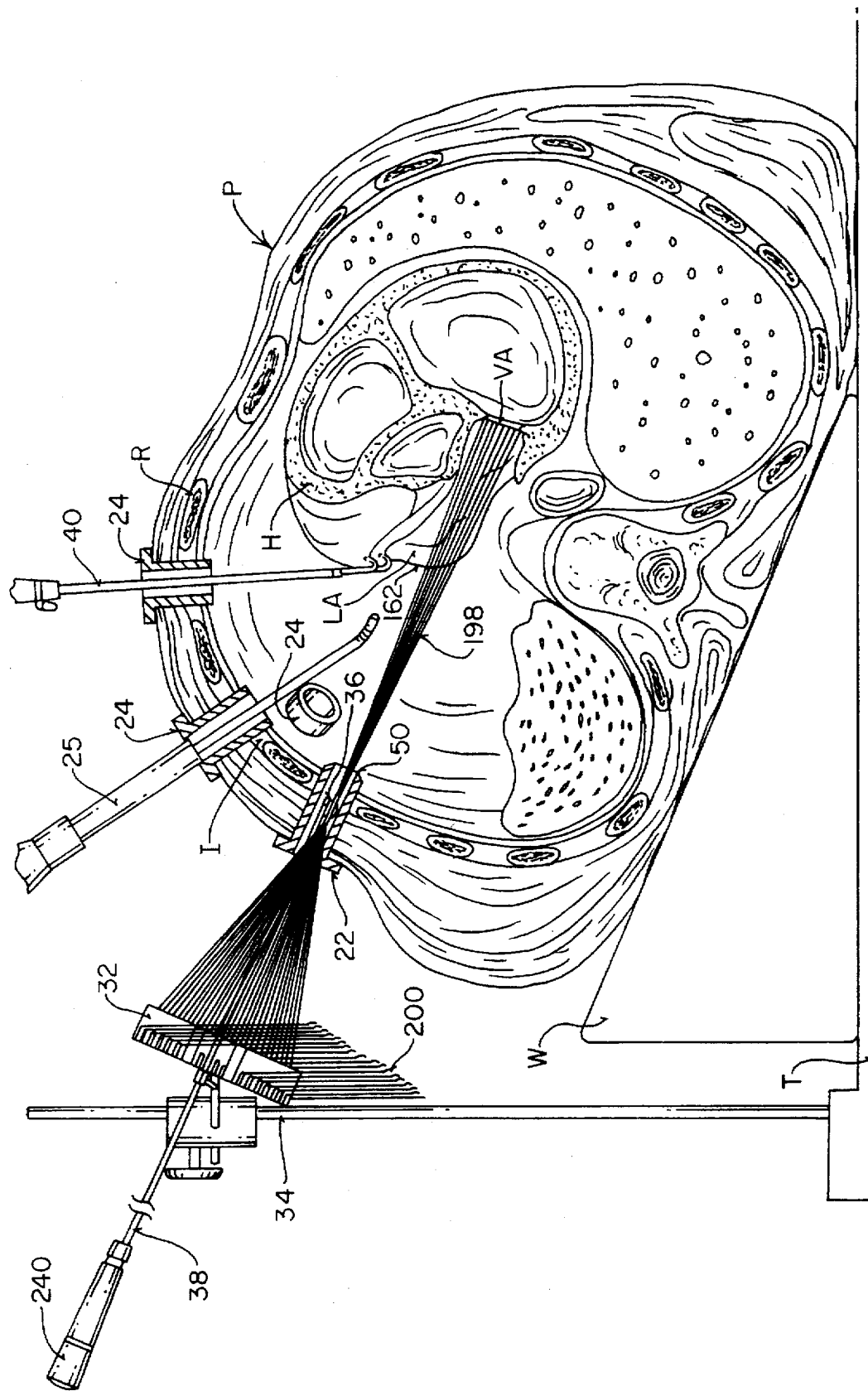
FIGS. 8A–8B are transverse cross-sectional views of the system and patient of FIG. 1 taken through the patient's thorax, showing the introduction of the replacement valve into the left atrium and the tying of knots in the sutures to secure the prosthesis in the patient's heart.

Referring now to FIG. 8A, replacement valve 36 may then be introduced into the left atrium LA by advancing introducer 38 through passage 50 of access cannula 22. Replacement valve 36 is oriented on introducer 38 so as to be introduced edge-first through passage 50. As replacement valve 36 is advanced into the thoracic cavity, organizing ring 32 maintains tension on sutures 198, allowing replacement valve 36 to slide along sutures 198. Introducer 38 is advanced through atriotomy 162 so that replacement valve 36 is disposed within left atrium LA. Replacement valve 36 is then pivoted on introducer 38 by rotating knob 240, so that sewing ring 228 of replacement valve 36 (FIG. 17A) may be aligned with valve annulus VA.

Figure 8B:
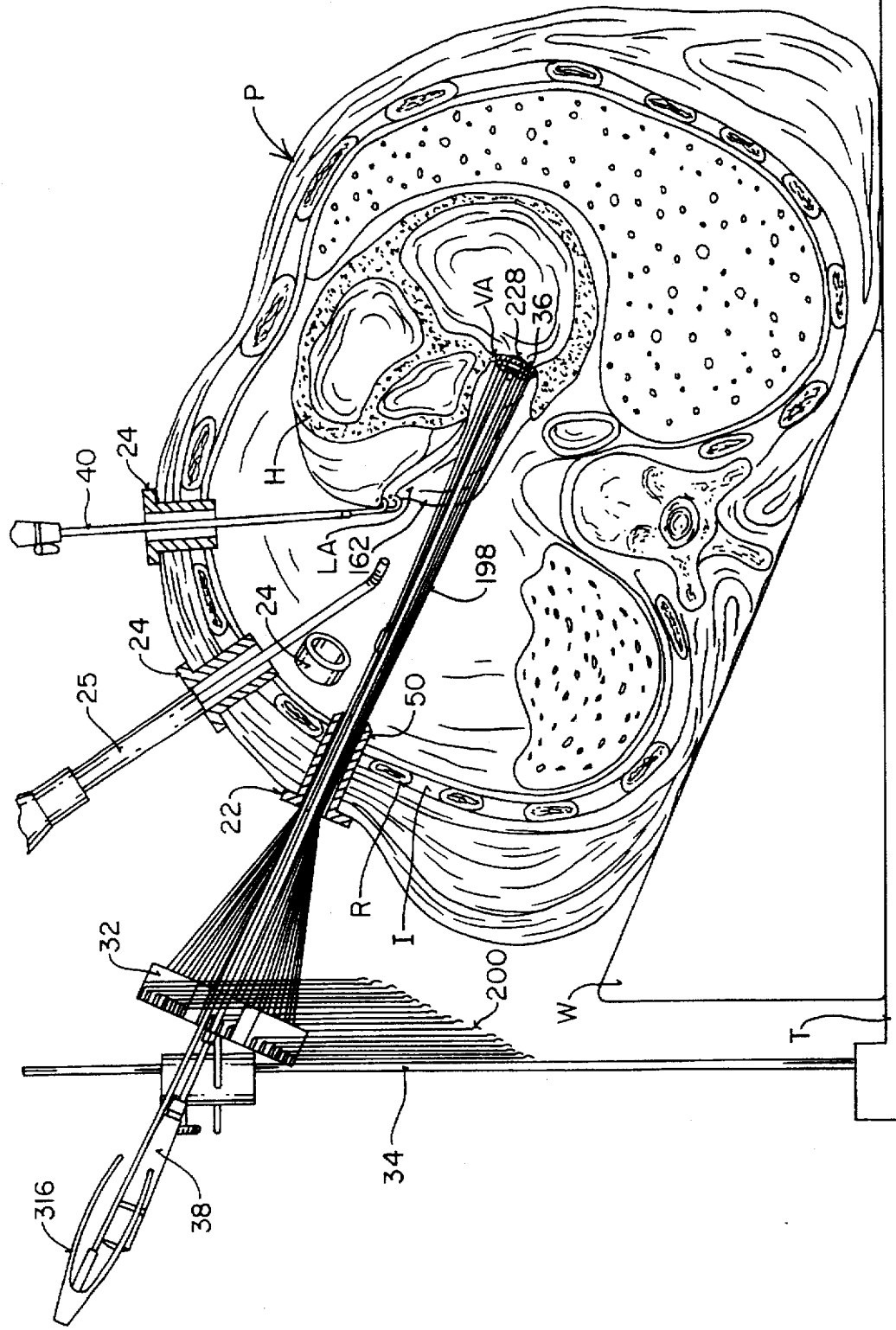

Introducer 38 is then advanced further into left atrium LA so as to position replacement valve 36 against or within valve annulus VA, as illustrated in FIG. 8B. Square or overhand knots are then formed in sutures 198 outside of the patient's thoracic cavity, and the knots are pushed by a knot pusher 316 through passage 50 and atriotomy 162 toward sewing ring 228 of replacement valve 36.

While knot pusher 316 may have a variety of configurations, an exemplary embodiment is illustrated in FIGS. 25A–25B. Knot pusher 316 comprises a shaft 318 having a distal end 320 and a proximal end 322, to which is connected an actuator 324 constructed like actuator 120 described above in connection With FIG. 12A. Actuator 324 translates a push rod 326 extending through shaft 318. A pair of movable jaws 328 are pivotally mounted to distal end 320 of shaft 318, and are coupled to push rod 326 such that proximal movement of push rod 326 opens jaws 328. A notch 330 at the distal end of each jaw 328 is configured to receive a suture 198.

In use, a first free end of a suture 198 is tied in a loop or slip knot over a second free end of suture 198, and jaws 328 are positioned just proximal to the knot. Jaws 328 are then opened such that each free end of suture 198 is positioned within a notch 330 at the distal end of jaws 328 and the slip knot is disposed centrally between jaws 328. While holding tension on the free ends of the sutures outside the thoracic cavity, knot pusher 316 is advanced distally, pushing the slip knot through passage 50 of access cannula 22 and atriotomy 162 until the slip knot engages sewing ring 228 of replacement valve 36.

Figure 9:
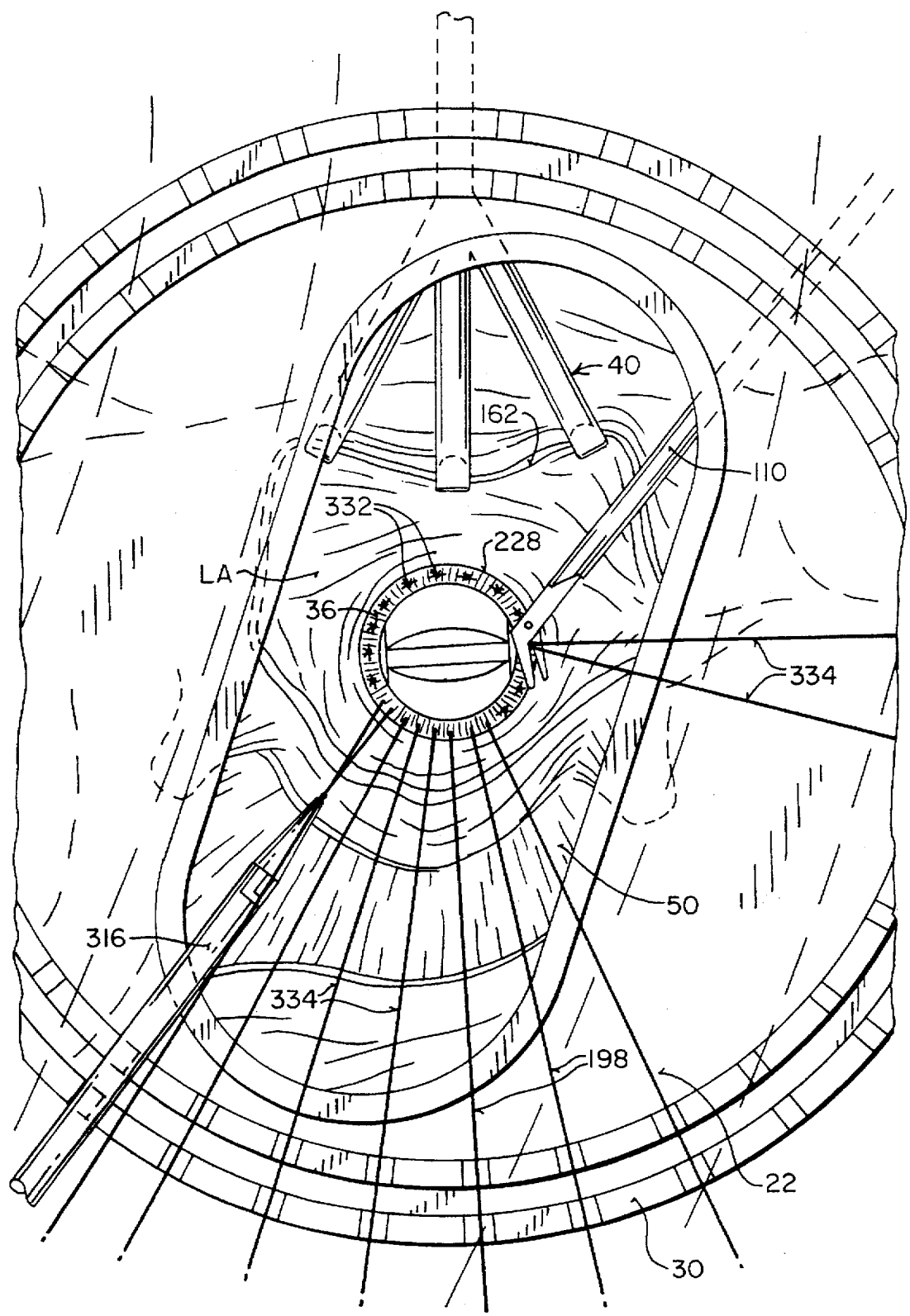
FIG. 9 is a top view looking into the patient's thoracic cavity through a passage of an access cannula in the system of FIG. 1, showing pushing the knots toward the replacement valve and trimming the free ends of the sutures.
Figure 10:
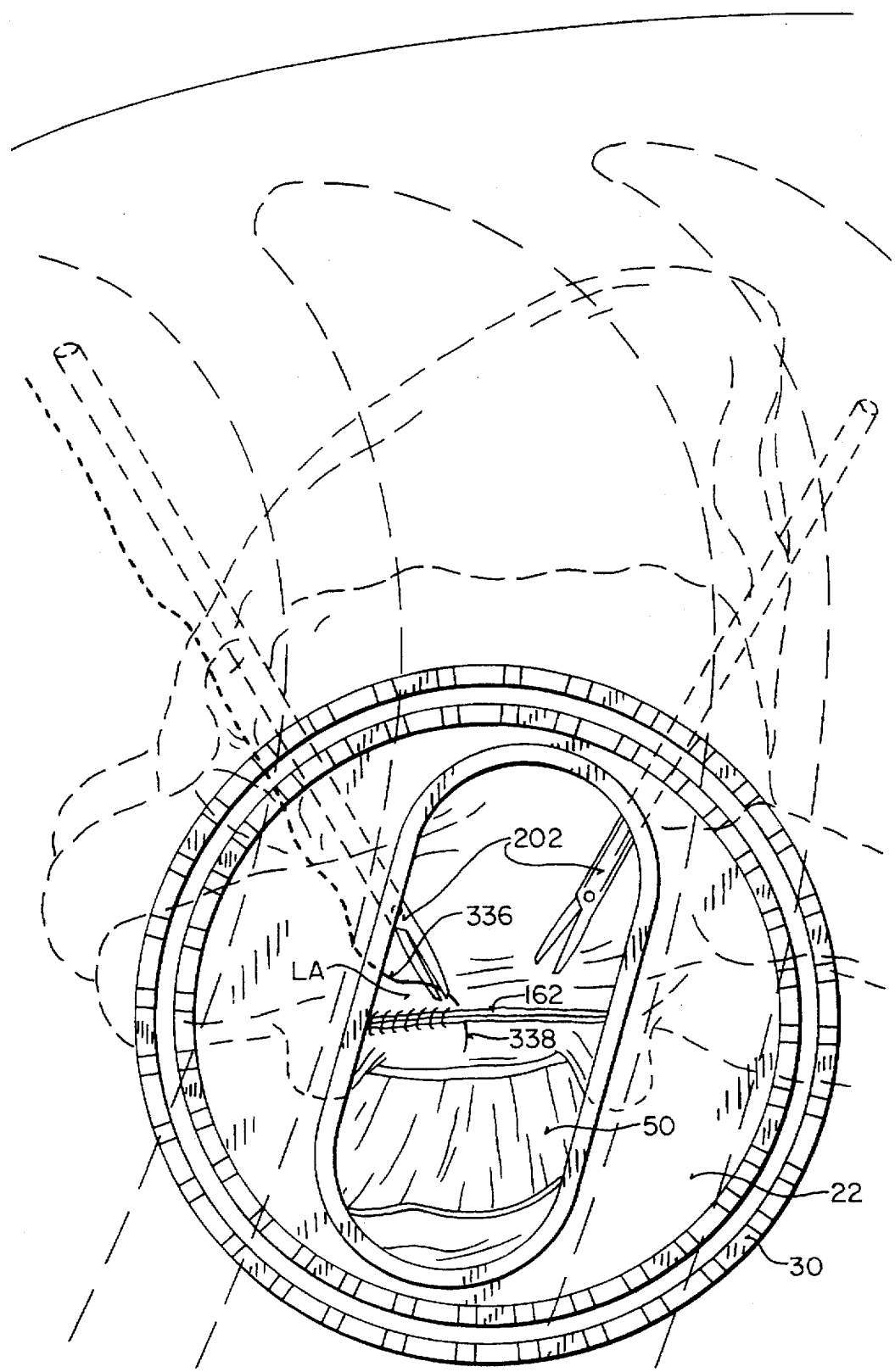
FIG. 10 is a top view looking into the patient's thoracic cavity through a passage of an access cannula in the system of FIG. 1, showing the closure of the patient's left atrium.

Referring now to FIG. 9, when a plurality of knots 332 (usually 5 to 8) have been tied and pushed against sewing ring 228 by knot pusher 316, knots 332 are cinched down tightly, and free ends 334 are trimmed using scissors 110 or other cutting device.

It will be understood to those of ordinary skill in the art that the thoracoscopic devices and methods disclosed above for tissue manipulation, retraction, cutting, suturing, and the like may be used to accomplish procedures such as annuloplasty, commissurotomy, quadrangular resection, shortening and reattachment of chordae tendonae, and various other valve repair procedures. To perform annuloplasty, valve annulus VA is contracted by suturing a portion of the valve annulus so as to overlap an adjacent portion, or by attaching a prosthetic annuloplasty device such as a Carpentier or Duran annuloplasty ring (not shown) to valve annulus VA to reduce its diameter. To perform commissurotomy, the valve leaflets VL are separated by cutting between them where they have fused together due to calcification or disease. To perform quadrangular resection, valve leaflets VL are shortened or narrowed by excising a portion of one or more leaflets VL, and reattaching the remaining portions of the leaflet by suturing. The chordae tendonae (not shown), which act as resilient springs between valve leaflets VL and the papillary muscles (not shown) attached to the heart wail in the left ventricle LV, may be shortened by excising a portion thereof and reattaching the ends of the remaining portions by suturing. Similarly, severed chordae tendonae may be restored by reattachment of the severed ends with sutures. Open-chest techniques for performing such procedures are described in detail in Kirklin and Barratt-Boyes, Cardiac Surgery, pp. 329–340, the disclosure of which has been incorporated herein by reference.

When the valve replacement or other surgical procedure in left atrium LA is completed, atriotomy 162 is closed. Sutures, thoracoscopic staples or other types of closure devices may be used for this purpose. In one embodiment, illustrated in FIG. 10, atriotomy 162 is closed by suturing, wherein needle drivers 202 are introduced through trocar sleeves 24 and/or access cannula 22, and a suture 336 having a needle 338 attached to an end thereof is used to sew up atriotomy 162 using conventional suturing techniques. Before and/or during closure, a suction/irrigation tube (not shown) is usually introduced through a trocar sleeve 24 and into left atrium LA or left ventricle LV to remove any air therein and to fill the heart chambers with a saline solution.

After atriotomy 162 has been closed, any remaining instruments are removed from the thoracic cavity. A chest tube may be introduced through one of trocar sleeves 24 to facilitate evacuation of the pleural cavity. Access cannula 22 and trocar sleeves 24 are then removed from the chest wail, and the incisions or penetrations through which they were introduced are closed, usually by suturing or stapling.

The patient's lung may then be reinflated, and cardiac function may be restarted. As described in copending application Ser. No. 07/991,188, now abandoned which has been incorporated herein by reference, infusion of cardioplegic fluid through aortic occlusion catheter 82 and/or retroperfusion catheter 102 is discontinued, and a saline solution is infused through one or both of these catheters to irrigate the heart and coronary arteries (see FIG. 3). The saline solution, along with blood, other fluids, air, thrombus, and other emboli within the heart or coronary arteries are then aspirated through the inner lumen of aortic occlusion catheter 82, as well as through venous cannula 70 and/or pulmonary venting catheter 79. Occlusion balloon 88 on aortic occlusion catheter 82 is then deflated, allowing warm, oxygenated blood to flow into the coronary arteries to perfuse the myocardium. Cardiac contractions will usually begin soon thereafter. In some cases, electrical defibrillation may be necessary to help restore cardiac function. Aortic occlusion catheter 82 and retroperfusion catheter 102 may then be removed from the patient. Cardiopulmonary bypass is then discontinued, and arterial cannula 78, venous cannula 70, and pulmonary venting catheter 79 are removed from the patient.

In addition to performing mitral valve repair and replacement, the techniques of the invention also facilitate surgical intervention into other regions of the heart and great vessels. The devices and methods described above may be used to form an opening directly into the left ventricle, right atrium, or right ventricle, or into a great vessel such as the aorta, superior vena cava, inferior vena cava, pulmonary artery, or pulmonary vein, for surgical intervention in such cavities. For example, a penetration may be made in the wall of the aorta, and the aortic valve may be repaired or replaced with a prosthesis, using techniques and devices like those described above for mitral valve replacement. Moreover, the devices and methods of the invention also facilitate intracardiac procedures such as repair of atrial or ventricular septal defects, electrophysiological mapping and ablation of the myocardium, myocardial drilling, and other procedures. Furthermore, devices may be introduced through an opening into the heart or great vessel and advanced therefrom into vessels such as the coronary arteries to perform procedures such as angioplasty, atherectomy, coronary artery bypass grafting, or treatment of aneurysms.

While the above is a complete description of the preferred embodiments of the invention, various alternatives, modifications and equivalents may be used. Therefore, the above description should not be taken as limiting the scope of the invention, which is defined by the appended claims.

What is claimed is:

1. A system for performing an interventional procedure in a heart within a patient's chest, the chest being defined by a plurality of ribs and a sternum, the system comprising:

a device for inducing cardioplegic arrest from outside the patient's chest;

a blood circulation device for maintaining circulation of oxygenated blood in the patient's arterial system downstream of the heart; and an interventional device positionable through a percutaneous penetration between two adjacent ribs and through a penetration in a wall of the heart for performing a surgical intervention within the heart, the interventional device being configured for manipulation entirely from outside the chest, the intervensional device also including a replacement valve, a valve delivery device, and an elongate handle, the replacement valve being configured to be positioned into the chest through a percutaneous penetration between two adjacent ribs, the valve delivery device being couplable to the replacement valve and configured for positioning the replacement valve between the ribs and into the heart, the elongated handle having distal and proximal ends, the distal end having a coupling configured to releasably hold the replacement valve, the coupling being pivotable relative to the handle.

2. The system of claim 1 wherein the replacement valve has an outer diameter and is configured to pass through a percutaneous penetration having a width smaller than the outer diameter.

3. The system of claim 1 wherein the valve delivery device has a handle defining a longitudinal axis, and wherein the replacement valve has a sewing ring for attachment to the heart, the sewing ring having a central axis, the valve delivery device being configured to position the valve through the percutaneous penetration with the central axis generally parallel to the longitudinal axis.

4. The system of claim 1 wherein the replacement valve is attached to a holder which is couplable to the valve delivery device.

5. The system of claim 4 wherein the holder and valve together have a first profile smaller than the percutaneous penetration.

6. The system of claim 5 wherein the holder and valve together have a second profile larger than the percutaneous penetration.

7. The system of claim 1 wherein the delivery device further comprises an actuator actuable from the proximal end for pivoting the coupling.

8. The system of claim 1 wherein the device for inducing cardioplegic arrest comprises an occlusion device for occluding the ascending aorta between the coronary arteries and the brachiocephalic artery.

9. The system of claim 8 wherein the occlusion device comprises an endoaortic catheter having proximal and distal ends, and an occluding member near the distal end configured to occlude the ascending aorta with the proximal end extending transluminally out of the chest through a peripheral artery.

10. The system of claim 9 further comprising a fluid delivery device for delivering cardioplegic fluid to the myocardium from outside the chest.

11. The system of claim 10 wherein the endoaortic catheter has a port near the distal end and an inner lumen extending from the proximal end to the port, the fluid delivery device being in communication with the inner lumen.

12. The system of claim 1 wherein the blood circulation device comprises a cardiopulmonary bypass system including a venous cannula positionable in a peripheral vein for withdrawing blood therefrom, an oxygenator for oxygenating the blood, and an arterial cannula positionable in a peripheral artery for returning the blood thereto.

* * * * *